(12) United States Patent
Woloschuk et al.

(10) Patent No.: US 10,709,847 B2
(45) Date of Patent: Jul. 14, 2020

(54) RETRACTABLE NEEDLE SYRINGE WITH UNITARY PROPELLANT RELEASE MODULE

(71) Applicant: L.O.M. Laboratories Inc., Vancouver (CA)

(72) Inventors: Ralph E. Woloschuk, St. Albert (CA); Scott E. Castanon, Carlsbad, CA (US); Warren Marc Terry, San Diego, CA (US)

(73) Assignee: L.O.M. Laboratories Inc., Vancouver (CA)

( * ) Notice: Subject to any disclaimer, the term of this patent is extended or adjusted under 35 U.S.C. 154(b) by 460 days.

(21) Appl. No.: 15/544,692

(22) PCT Filed: Jan. 19, 2016

(86) PCT No.: PCT/CA2016/050041
§ 371 (c)(1),
(2) Date: Jul. 19, 2017

(87) PCT Pub. No.: WO2016/115628
PCT Pub. Date: Jul. 28, 2016

(65) Prior Publication Data
US 2017/0368267 A1 Dec. 28, 2017

Related U.S. Application Data

(60) Provisional application No. 62/105,624, filed on Jan. 20, 2015.

(51) Int. Cl.
*A61M 5/32* (2006.01)
*A61M 5/31* (2006.01)
(Continued)

(52) U.S. Cl.
CPC ........ *A61M 5/3232* (2013.01); *A61M 5/3202* (2013.01); *A61M 5/3221* (2013.01);
(Continued)

(58) Field of Classification Search
CPC .. A61M 5/3232; A61M 5/322; A61M 5/3234; A61M 5/3293; A61M 5/508;
(Continued)

(56) References Cited

U.S. PATENT DOCUMENTS

| 4,978,340 A | 12/1990 | Terrill |
| 5,098,390 A | 3/1992 | Wallingford |

(Continued)

FOREIGN PATENT DOCUMENTS

| CA | 2291600 A1 | 11/1998 |
| CA | 2332918 A1 | 12/1999 |

(Continued)

OTHER PUBLICATIONS

Maxxon Applauds New Federal Needlestick Act Press Release, Nov. 2, 2000, Business Wire.

(Continued)

*Primary Examiner* — Rebecca E Eisenberg
*Assistant Examiner* — Tasnim Mehjabin Ahmed
(74) *Attorney, Agent, or Firm* — Oyen Wiggs Green & Mutala LLP

(57) ABSTRACT

A modular retractable needle assembly having a unitary propellant release structure is provided. The modular retractable needle assembly can be coupled to a suitable syringe. A modular filler needle can be provided that is engageable to the syringe. Kits comprising the modular retractable needle assembly, one or more syringes, and a modular filler needle are provided.

20 Claims, 14 Drawing Sheets

(51) Int. Cl.
  *A61M 5/34* (2006.01)
  *A61M 5/315* (2006.01)
  *A61M 5/50* (2006.01)

(52) U.S. Cl.
  CPC .......... *A61M 5/3286* (2013.01); *A61M 5/347* (2013.01); *A61M 5/31511* (2013.01); *A61M 5/5013* (2013.01); *A61M 2005/3123* (2013.01); *A61M 2005/323* (2013.01); *A61M 2005/3239* (2013.01); *A61M 2205/586* (2013.01)

(58) Field of Classification Search
  CPC .. A61M 2005/3241; A61M 2005/3236; A61M 2005/3235; A61M 2005/3239; A61M 2005/3231; A61M 2005/3242; A61M 2005/3123
  See application file for complete search history.

(56) References Cited

U.S. PATENT DOCUMENTS

| | | |
|---|---|---|
| 5,118,614 A | 6/1992 | Rybak |
| 5,120,310 A | 6/1992 | Shaw |
| 5,122,118 A | 6/1992 | Haber |
| 5,176,640 A | 1/1993 | Nacci |
| 5,188,614 A | 2/1993 | Hart |
| 5,211,628 A | 5/1993 | Marshall |
| 5,224,936 A | 7/1993 | Gallagher |
| 5,279,580 A | 1/1994 | Wallingford |
| 5,334,155 A | 8/1994 | Sobel |
| 5,360,404 A * | 11/1994 | Novacek ............. A61M 5/3202 604/110 |
| 5,389,076 A | 2/1995 | Shaw |
| 5,407,436 A | 4/1995 | Toft |
| 5,423,758 A | 6/1995 | Shaw |
| 5,433,712 A | 7/1995 | Stiles |
| 5,533,970 A | 7/1996 | Berger |
| 5,575,777 A | 11/1996 | Cover |
| 5,578,011 A | 11/1996 | Shaw |
| 5,632,733 A | 5/1997 | Shaw |
| 5,702,367 A | 12/1997 | Cover |
| 5,716,341 A * | 2/1998 | Saito .................... A61M 5/322 604/110 |
| 5,779,679 A | 7/1998 | Shaw |
| 5,797,880 A | 8/1998 | Erskine |
| 5,810,775 A | 9/1998 | Shaw |
| 5,845,957 A | 12/1998 | Hurst |
| 5,868,713 A | 2/1999 | Klippenstein |
| 5,882,342 A | 3/1999 | Cooper |
| 5,935,104 A | 8/1999 | Janek |
| 5,989,220 A | 11/1999 | Shaw |
| 5,997,512 A | 12/1999 | Shaw |
| 6,015,438 A | 1/2000 | Shaw |
| 6,077,245 A | 6/2000 | Heinrich |
| 6,083,199 A | 7/2000 | Thorley |
| 6,086,568 A | 7/2000 | Caizza |
| 6,090,077 A | 7/2000 | Shaw |
| 6,099,500 A * | 8/2000 | Dysarz ................ A61M 5/3234 604/110 |
| 6,179,812 B1 | 1/2001 | Botich |
| 6,183,440 B1 | 2/2001 | Bell |
| 6,193,695 B1 | 2/2001 | Rippstein |
| 6,206,853 B1 | 3/2001 | Bonnet |
| 6,210,371 B1 | 4/2001 | Shaw |
| 6,221,055 B1 | 4/2001 | Shaw |
| 6,241,707 B1 | 6/2001 | Dysarz |
| 6,267,749 B1 | 7/2001 | Miklos |
| 6,361,525 B2 | 3/2002 | Capes |
| 6,406,461 B1 | 6/2002 | Ellingsen |
| 6,409,701 B1 | 6/2002 | Cohn |
| 6,413,236 B1 | 7/2002 | Van Dyke |
| 6,413,237 B1 | 7/2002 | Caizza |
| 6,432,087 B1 | 8/2002 | Hoeck |
| 6,458,105 B1 | 10/2002 | Rippstein |
| 6,474,472 B1 | 11/2002 | Shaw |
| 6,494,863 B1 | 12/2002 | Shaw |
| 6,558,357 B1 | 5/2003 | Hoeck |
| 6,572,565 B2 | 6/2003 | Daley |
| 6,572,584 B1 | 6/2003 | Shaw |
| 6,585,690 B1 | 7/2003 | Hoeck |
| 6,599,268 B1 | 7/2003 | Townsend |
| 6,679,863 B2 | 1/2004 | Bush |
| 6,692,470 B2 | 2/2004 | Sanpietro |
| 6,740,062 B2 | 5/2004 | Hjertman |
| 6,767,335 B1 | 7/2004 | Helg |
| 6,846,301 B2 | 1/2005 | Smith |
| 6,868,713 B2 | 3/2005 | Bolz |
| 6,872,193 B2 | 3/2005 | Shaw |
| RE39,107 E | 5/2006 | Shaw |
| 7,090,656 B1 | 8/2006 | Botich |
| 7,182,734 B2 | 2/2007 | Saulenas |
| 7,258,678 B2 | 8/2007 | Wilkinson |
| 7,294,118 B2 | 11/2007 | Saulenas |
| 7,303,547 B2 | 12/2007 | Pressly, Sr. |
| 7,344,517 B2 | 3/2008 | Schiller |
| 7,351,224 B1 | 4/2008 | Shaw |
| D617,453 S | 6/2010 | Shaw |
| D617,454 S | 6/2010 | Shaw |
| 7,740,615 B2 | 6/2010 | Shaw |
| 7,803,132 B2 | 9/2010 | Janek |
| 7,811,259 B2 | 10/2010 | Klippenstein |
| 7,846,135 B2 | 12/2010 | Runfola |
| D645,962 S | 9/2011 | Shaw |
| 8,048,031 B2 | 11/2011 | Shaw |
| D660,420 S | 5/2012 | Shaw |
| 8,167,848 B2 | 5/2012 | Klippenstein |
| 8,469,927 B2 | 6/2013 | Shaw |
| 8,496,600 B2 | 7/2013 | Shaw |
| 8,523,810 B2 | 9/2013 | Klippenstein |
| 8,535,267 B2 | 9/2013 | Caizza |
| 8,574,193 B2 | 11/2013 | Caizza |
| 8,758,296 B2 | 6/2014 | Woehr et al. |
| 8,777,504 B2 | 7/2014 | Shaw |
| 9,138,545 B2 | 9/2015 | Shaw |
| 9,192,732 B2 | 11/2015 | Klippenstein |
| 9,408,983 B2 | 8/2016 | Klippenstein |
| 9,649,450 B2 | 5/2017 | Klippenstein |
| 10,195,364 B2 | 2/2019 | Andersen |
| 2003/0004491 A1 | 1/2003 | Tenhuisen |
| 2003/0040717 A1 | 2/2003 | Saulenas |
| 2003/0078540 A1 | 4/2003 | Saulenas |
| 2003/0176843 A1 | 9/2003 | Wilkinson |
| 2004/0153034 A1 | 8/2004 | Fan |
| 2005/0159705 A1 | 7/2005 | Crawford |
| 2005/0159707 A1 | 7/2005 | Schiller |
| 2005/0215951 A1 | 9/2005 | Saulenas |
| 2006/0084919 A1 | 4/2006 | Shaw |
| 2006/0111671 A1 * | 5/2006 | Klippenstein ....... A61M 5/3293 604/110 |
| 2007/0260189 A1 | 11/2007 | Shaw |
| 2008/0119786 A1 | 5/2008 | Stewart |
| 2008/0132851 A1 | 6/2008 | Shaw |
| 2008/0208122 A1 | 8/2008 | Walton |
| 2008/0221517 A1 | 9/2008 | Shaw |
| 2009/0306601 A1 | 12/2009 | Shaw |
| 2010/0000040 A1 | 1/2010 | Shaw |
| 2010/0125252 A1 | 5/2010 | Tseng |
| 2010/0222739 A1 | 9/2010 | Klippenstein |
| 2011/0021989 A1 | 1/2011 | Janek |
| 2011/0064512 A1 | 3/2011 | Shaw |
| 2011/0125097 A1 | 5/2011 | Shaw |
| 2011/0213304 A1 | 9/2011 | Schraga |
| 2011/0230844 A1 | 9/2011 | Shaw |
| 2012/0004621 A1 | 1/2012 | Shaw |
| 2012/0184903 A1 | 7/2012 | Klippenstein |
| 2012/0259243 A1 | 10/2012 | Shaw |
| 2012/0323181 A1 | 12/2012 | Shaw |
| 2013/0261551 A1 | 10/2013 | Shaw |
| 2013/0345632 A1 | 12/2013 | Klippenstein |
| 2014/0012206 A1 | 1/2014 | Shaw |
| 2014/0171876 A1 | 6/2014 | Shaw |
| 2014/0171877 A1 | 6/2014 | Shaw |
| 2014/0276435 A1 | 9/2014 | Shaw |
| 2014/0276445 A1 | 9/2014 | Shaw |

(56) References Cited

U.S. PATENT DOCUMENTS

| | | | |
|---|---|---|---|
| 2015/0073303 A1 | 3/2015 | Shaw | |
| 2015/0283329 A1 | 10/2015 | Shaw | |
| 2016/0045676 A1 | 2/2016 | Klippenstein | |
| 2017/0100548 A1 | 4/2017 | Andersen | |
| 2018/0042539 A1* | 2/2018 | Woloschuk | A61B 5/150389 |

FOREIGN PATENT DOCUMENTS

| | | |
|---|---|---|
| CA | 2437415 A1 | 2/2002 |
| CA | 2455160 A1 | 6/2004 |
| CA | 2495571 A1 | 6/2004 |
| CA | 2548722 A1 | 6/2005 |
| CA | 2651037 A1 | 11/2007 |
| CA | 2713152 A1 | 8/2009 |
| CA | 2724197 A1 | 12/2009 |
| CA | 2728548 A1 | 1/2010 |
| CA | 2744433 A1 | 6/2010 |
| CA | 2758026 A1 | 11/2010 |
| CA | 2785561 A1 | 8/2011 |
| CA | 2802547 A1 | 1/2012 |
| CA | 2809510 A1 | 2/2012 |
| CA | 2818325 A1 | 5/2012 |
| CN | 2853080 Y | 1/2007 |
| CN | 101193675 A | 4/2008 |
| EP | 479217 A1 | 4/1992 |
| EP | 596211 A1 | 5/1994 |
| FR | 2831448 A1 | 5/2003 |
| JP | 6142204 A | 5/1994 |
| NL | 9000292 A | 9/1991 |
| WO | 91/04760 A1 | 4/1991 |
| WO | 92/05818 | 4/1992 |
| WO | 93/18810 A1 | 9/1993 |
| WO | 95/01811 A1 | 1/1995 |
| WO | 96/35463 A1 | 11/1996 |
| WO | 98/34659 A1 | 8/1998 |
| WO | 99/25401 A1 | 5/1999 |
| WO | 00/02607 A1 | 1/2000 |
| WO | 00/057940 A1 | 10/2000 |
| WO | 00/061061 A2 | 10/2000 |
| WO | 01/024852 A1 | 4/2001 |
| WO | 01/080930 A1 | 11/2001 |
| WO | 02/011796 A1 | 2/2002 |
| WO | 03/051435 A1 | 6/2003 |
| WO | 2004/050138 A2 | 6/2004 |
| WO | 2004/060451 A1 | 7/2004 |
| WO | 2004/082747 A1 | 9/2004 |
| WO | 2005/011792 A1 | 2/2005 |
| WO | 2005/058399 A1 | 6/2005 |
| WO | 2005/070292 A1 | 8/2005 |
| WO | 2005/072801 A1 | 8/2005 |
| WO | 2006/017889 A1 | 2/2006 |
| WO | 2006/024172 A1 | 3/2006 |
| WO | 2006/044010 A2 | 4/2006 |
| WO | 2006/108243 A2 | 10/2006 |
| WO | 2006/119570 A1 | 11/2006 |
| WO | 2007/131086 A2 | 11/2007 |
| WO | 2009/102624 A1 | 8/2009 |
| WO | 2009/151704 A1 | 12/2009 |
| WO | 2010/002757 A1 | 1/2010 |
| WO | 2010/065375 A1 | 6/2010 |
| WO | 2010/132196 A1 | 11/2010 |
| WO | 2011/066022 A1 | 6/2011 |
| WO | 2011/100039 A1 | 8/2011 |
| WO | 2012/003343 A1 | 1/2012 |
| WO | 2012/015644 A1 | 2/2012 |
| WO | 2012/067778 A1 | 5/2012 |
| WO | 2012/162821 A1 | 12/2012 |
| WO | 2012/174109 A1 | 12/2012 |
| WO | 2013/126819 A1 | 8/2013 |
| WO | 2014/093026 A1 | 6/2014 |
| WO | 2014/143220 A1 | 9/2014 |
| WO | 2014/143221 A1 | 9/2014 |
| WO | 2015/034548 A1 | 3/2015 |
| WO | 2015/034549 A1 | 3/2015 |
| WO | 2015/080724 A1 | 6/2015 |
| WO | 2015145207 A1 | 10/2015 |
| WO | 2016/115628 A1 | 7/2016 |

OTHER PUBLICATIONS

Maxxon Safety Syringe Press Release, Feb. 2000, online: <http://www.micro-stocks.com/Research/MXON.htm>.

Maxxon Announces Safety Syringe Patent Filing, Advance for Respiratory Care Practitioner, Daily News Watch, Feb. 2000, online:<http://www.advanceforrcp.com/previousdnw/rcdnwjan31.html>.

* cited by examiner

RETRACTABLE NEEDLE SYRINGE WITH UNITARY PROPELLANT RELEASE MODULE

CROSS-REFERENCE TO RELATED APPLICATIONS

This application is a 371 national phase entry of Patent Cooperation Treaty patent application No. PCT/CA2016/050041, which claims priority to, and the benefit of, U.S. provisional patent application No. 62/105,624 filed 20 Jan. 2015. Both of these applications are incorporated by reference herein in their entirety.

TECHNICAL FIELD

Some embodiments of the present invention pertain to propellant release devices for use in pneumatically actuated medical devices. Some embodiments of the present invention pertain to modular needle assemblies that include a propellant release device for use in pneumatically actuated medical devices.

BACKGROUND

It is well known that many dangerous communicable diseases are spread through contacting the body fluids of an infected person. After use of a sharps-containing medical device, residual body fluids are likely to remain on or within the sharp element of the medical device, for example needles or blades. After use, the sharp element should be covered, to prevent it from accidentally stabbing the person who is using the medical device, thereby potentially releasing residual bodily fluids into such a person. While caps can be used to cover sharps elements after use, there remains a risk that persons attempting to cap the sharp element may misapply the cap and accidentally pierce their skin with the used sharp element, resulting in potential exposure to communicable diseases.

Accordingly, it is desirable to provide for retraction of a sharps element inside of a medical device after the medical device has been used. For example, syringes having retractable needles are known, and syringes having pneumatically actuated retractable needles have been developed, as exemplified by U.S. Pat. Nos. 5,868,713 and 7,811,259, and Patent Cooperation Treaty patent application No. PCT/CA2015/051113, each of which is incorporated by reference herein. Often, such retractable needle syringes are provided as prefilled syringes. Modular needle assemblies designed to work with such retractable needles have also been developed, wherein the modular needle assembly can be fitted to a syringe of any desired size, for example as described in Patent Cooperation Treaty publication No. WO 2012/162821, which is incorporated by reference herein.

There remains a need to provide pneumatically actuated medical devices that are easier and/or less expensive to construct.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a modular retractable needle assembly for engagement with a barrel of a retractable needle syringe having a plunger is provided. The modular retractable needle assembly has a body having an upper chamber at a proximal end thereof, a propellant chamber defined within the body, a seal sealingly engaged over the propellant chamber to seal a propellant in the propellant chamber, a retention member initially engaged within the upper chamber, the retention member being moveable in a distal direction in response to the application of a post-injection force to the plunger by a user, a needle hub initially engaged within the retention member, the needle hub being engageable with a retractable locking tip of the plunger upon the application of the post-injection force to the plunger by the user, a needle for injecting medicament into a patient engaged with the needle hub and projecting distally from the body, and a rupturing member projecting in the distal direction, the rupturing member being moveable in the distal direction in response to the application of the post-injection force to the plunger by the user to rupture the seal and thereby release propellant into the upper chamber. The outer surface of the body of the modular retractable needle assembly can be provided with engagement members for engaging the body with the barrel.

In one aspect, a modular filler needle assembly for engagement with a barrel of a syringe is provided. The modular filler needle assembly has a base engageable with the barrel, a support disc spaced apart from the base and positioned to provide a sealing engagement with the barrel, and a needle supported on the support disc for loading medicament into the syringe, the needle projecting distally from the base. The base can have engagement members on an outer surface thereof for engaging with the barrel. The support disc can be spaced apart from the base by a sufficient distance to allow the modular filler needle assembly to be secured on a syringe having a distal cavity for receiving a modular retractable needle assembly as described in this specification.

In one aspect, a syringe for use with a modular retractable needle assembly as described in this specification, or with a modular filler needle assembly as described in this specification, is provided. The syringe has a barrel, a plunger slideable within the barrel for loading or injecting medicament from a medicament chamber of the barrel, the plunger having a retraction lumen therein for receiving a needle retracted from the modular retractable needle assembly, a locking tip initially engaged within the retraction lumen, the locking tip being engageable with a needle hub of the modular retractable needle assembly upon application of a post-injection force by a user, the locking tip being retractable into the retraction lumen when a propellant chamber of the modular retractable needle assembly is ruptured, and a recess at a distal end of the barrel for receiving a modular needle assembly or a modular filler needle assembly as described in this specification.

In other aspects, kits having one or more syringes as described in this specification and at least one modular retractable needle assembly as described in this specification are provided. The kit can contain a modular filler needle assembly as described in this specification.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

In this specification, "seals" or "sealingly engages" means that two elements are engaged with sufficient sealing capability that the function for which the sealing is provided can be effectively performed.

"Distal" means the direction towards the tip of the needle when the syringe assembly is in the assembled state. "Proximal" means the direction opposite of distal, i.e. the direction away from the tip of the needle when the syringe assembly is in the assembled state.

"Downstream" means a direction in the distal direction, i.e. towards the tip of the needle, referring to the conventional direction of injection of medicament into a patient. "Upstream" means a direction opposite to downstream, i.e. in the proximal direction, e.g. in the direction of fluid flow when medicament is being drawn from a supply vial into the syringe for subsequent injection.

"Inwardly" means in a direction towards the axial centerline of the syringe. "Outwardly" means in a direction towards the outside of the syringe, i.e. away from the axial centerline of the syringe.

"Injection force" means a force that would typically be applied by a user to the plunger of a syringe to inject a medicament into a patient.

"Post-injection force" means a force that is applied to activate the propellant-actuated retraction mechanism described below after a user has completed injection of the medicament. In some embodiments, the post-injection force is greater than the injection force.

"Loading force" means a force typically applied by a user when drawing medicament into a syringe in preparation for administering that medicament to a patient.

Figure 1:
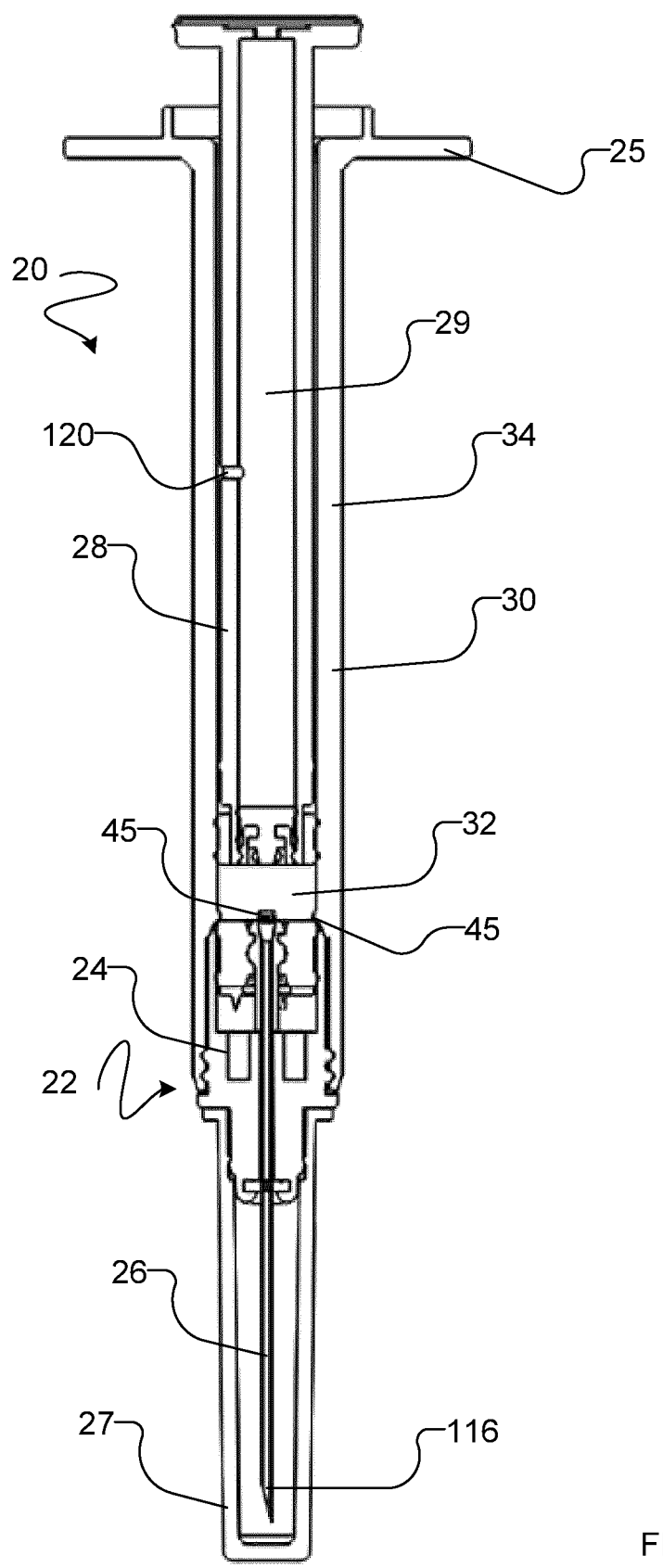
FIG. 1 is a cross-sectional view of a pneumatically-actuated retractable needle syringe having a modular needle assembly according to one example embodiment.

With reference to FIG. 1, an example embodiment of a retractable needle syringe 20 having a modular needle assembly 22 containing a unitary propellant release structure 24 is illustrated. Retractable needle syringe 20 has a hypodermic needle 26 at its distal end for use in administration of a medicament to a patient. A plunger 28 is slideably engaged within the barrel 30 of the syringe, to force medicament from a medicament chamber 32 (defined within syringe barrel 30 downstream of plunger 28 and upstream of needle 26) through needle 26 and into a patient.

A retraction lumen 29 is provided within plunger 28 for receiving the needle 26 following needle retraction. A cap 27 is provided for initially covering needle 26 prior to use. In some embodiments, cap 27 is provided with a roughened surface, a plurality of longitudinally extending ridges, or other surface features that make it easier for a user to twist modular needle assembly 22 onto syringe body 34. Syringe body 34 is provided with a flange 25 formed therewith or attached thereto at its proximal end, to facilitate grasping and usage of syringe assembly 20 by a user.

Figure 2:
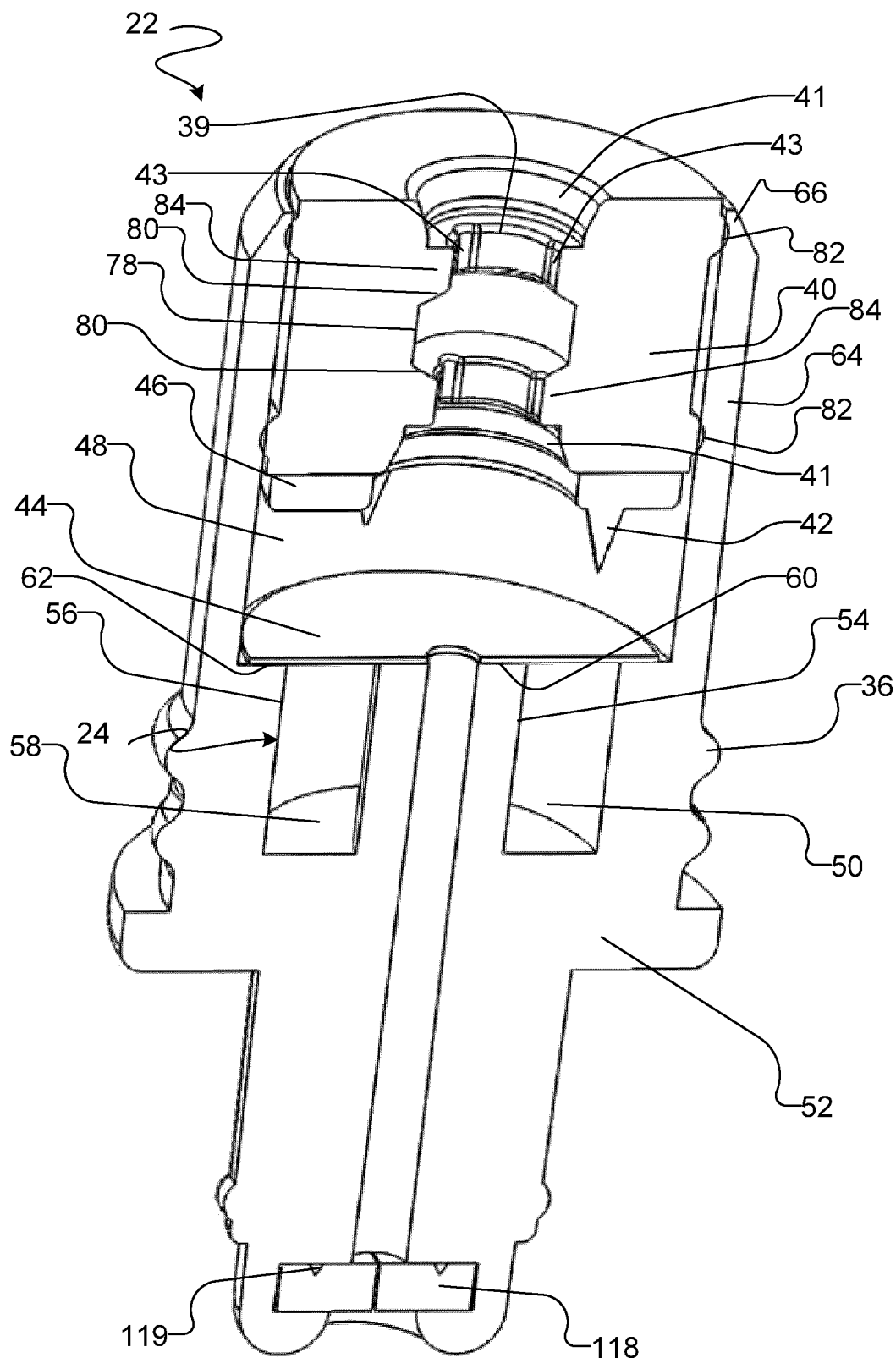
FIG. 2 is a partial cross-sectional view of the modular needle assembly of the example embodiment of FIG. 1, with the needle and needle hub omitted for clarity.

FIG. 2 shows the modular needle assembly 22 in more detail, with needle 26 and the needle hub 70 (described below) omitted for clarity. The surface of modular needle assembly 22 is provided with engagement members for engaging modular needle assembly 22 with the body 34 of syringe barrel 30. The distal surface of syringe body 34 is provided with corresponding engagement members, to allow a user to securely couple modular needle assembly 22 with syringe body 34. In the illustrated embodiment, modular needle assembly 22 is provided with outwardly projecting threads 36 on its external surface. Threads 36 are engageable with a corresponding set of threaded grooves 38 (FIG. 3A) provided on the distal internal surface of the distal cavity 37 of syringe body 34, to secure modular needle assembly 22 to syringe body 34. In alternative embodiments, the engagement of threads 36 and threaded grooves 38 could be replaced by a Luer lock fitting, which is a commonly used mechanism for sealingly engaging two components of a medical fluid delivery system. In some embodiments, including the illustrated embodiment, recessed threaded grooves 38 are used on the distal internal surface of syringe body 34 rather than inwardly projecting threads to minimize any interference that might be caused by inward projections on the distal internal surface of syringe body 34 as modular needle assembly 22 is inserted onto syringe body 34.

Modular needle assembly 22 includes a retaining member, which in the illustrated embodiment is a false wall 40, for supporting needle 26 (via a needle hub as described below) and one or more distally projecting rupturing members 42 for rupturing a seal 44 containing a propellant within unitary propellant release structure 24 when needle 26 is to be retracted. In the illustrated embodiment, distally projecting rupturing members 42 are formed integrally with a disc-like base 46 as a rigid substrate, and false wall 40 is formed as an elastomeric overmold of this rigid substrate. In alternative embodiments, any suitable method can be used to manufacture rupturing members 42 and false wall 40, and these can be joined together in any suitable manner, for example using adhesives, suitable fasteners, or the like. In alternative embodiments, rupturing members 42 and false wall 40 are not joined together, for example false wall 40 and disc-like base 46 bearing rupturing members 42 are pressed inside the interior surface of the upper chamber 48 of modular needle assembly 22 with a friction fit to secure these elements in place.

In some embodiments, disc-like base 46 is not in contact with false wall 40 when modular needle assembly 22 is assembled, however, those skilled in the art will recognize that it will be easier to manufacture and provide greater consistency in embodiments in which rupturing members 42 and false wall 40 are not joined together to insert disc-like base 46 into modular needle assembly 22 so that it contacts false wall 40 and is securely retained in that position prior to the application of a post-injection force by a user.

Unitary propellant release structure 24 is provided within modular needle assembly 22. In the illustrated embodiment, unitary propellant release structure 24 is formed as a generally cylindrical channel 50 defined within an interior portion of the body 52 of modular needle assembly 22. In the illustrated embodiment, cylindrical channel 50 is positioned distally of upper chamber 48 of modular needle assembly 22. Cylindrical channel 50 is defined by an inside cylindrical wall 54, an outside cylindrical wall 56, and a base 58 provided in body 52 of modular needle assembly 22.

Propellant is sealed within unitary propellant release structure 24 by a seal 44, which extends over cylindrical channel 50 at the proximal end thereof. In the illustrated embodiment, seal 44 is sealingly engaged with upper proximal edges 60, 62 of inside wall 54 and outside wall 56, respectively. Seal 44 can be secured to upper proximal edges 60, 62 in any suitable manner, for example by heat sealing, ultrasonic welding, the use of suitable adhesives, or the like.

In use, the application of a post-injection force moves false wall 40 and rupturing members 42 in the distal direction, causing rupturing members 42 to rupture seal 44, thereby releasing propellant into the upper chamber 48 of modular needle assembly 22. The composition, pressure and volume of propellant contained within unitary propellant release structure 24 by seal 44 should be sufficient to ensure that needle 26 is fully retracted when seal 44 is punctured, under a range of anticipated operating conditions.

In some embodiments, the use of a unitary propellant release structure 24 can facilitate the more efficient and/or less expensive manufacture and assembly of modular needle assembly 22 as compared with the use of a separate propellant release cell, for example as described in Patent Cooperation Treaty patent publication No. WO 2012/162821.

A perimeter wall 64 of modular needle assembly 22 extends proximally from channel 50, to define the upper chamber 48 of modular needle assembly 22. In the illustrated embodiment, perimeter wall 64 extends proximally from the outer circumference of upper proximal edge 62 of outside wall 56, so that upper proximal edge 62 is inset or recessed within perimeter wall 64. In the illustrated embodiment, upper proximal edges 60 and 62 are located at approximately the same distance in the distal direction from the body 52 of modular needle assembly 22, which can facilitate sealing of seal 44 over channel 50.

In the illustrated embodiment, the proximal portion of the outside surface of perimeter wall 64 is provided with an inwardly tapered portion 66, which tapers inwardly in the proximal direction from the outside circumference of perimeter wall 64. In use, inwardly tapered portion 66 engages with a correspondingly tapered surface 68 (FIG. 3B) provided on syringe body 34, to help sealingly engage modular needle assembly 22 with syringe body 34. In alternative embodiments, other sealing structures could be used to sealingly engage modular needle assembly 22 within syringe barrel 30. For example, an O-ring type seal or other compressible member could be compressed between the proximal portion of the outside surface of perimeter wall 64 and a lip formed on the inside surface of distal cavity 37 in place of correspondingly tapered surface 68, or the force with which the two components are engaged could be sufficiently strong to provide a sealing engagement therebetween without using an O-ring seal or other compressible member therebetween.

Figure 3A:
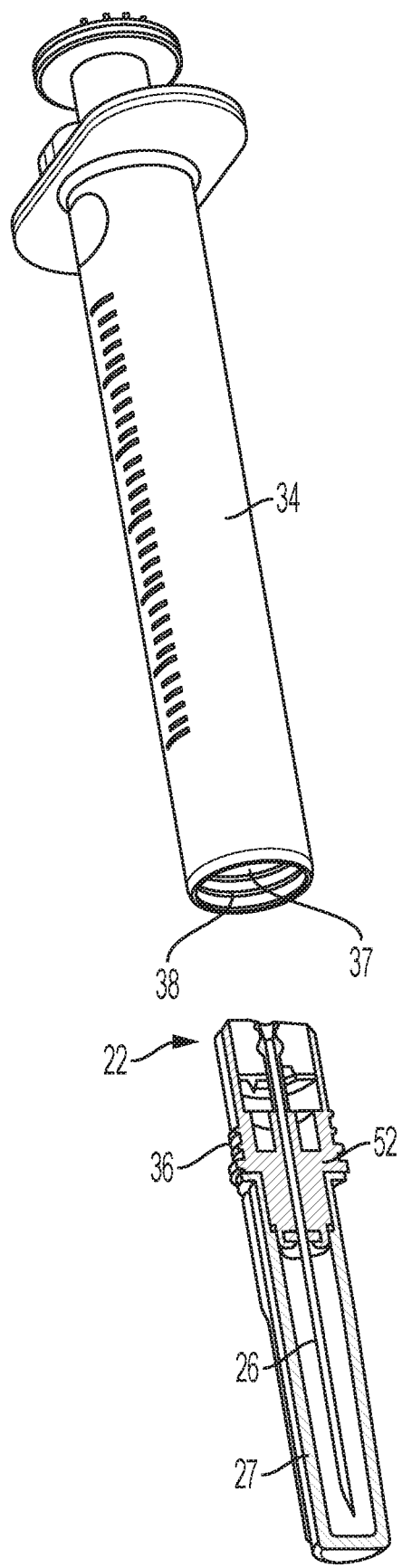
FIG. 3A is a perspective view of a syringe body that is engageable with a modular needle assembly, shown in cross-section.
Figure 3B:
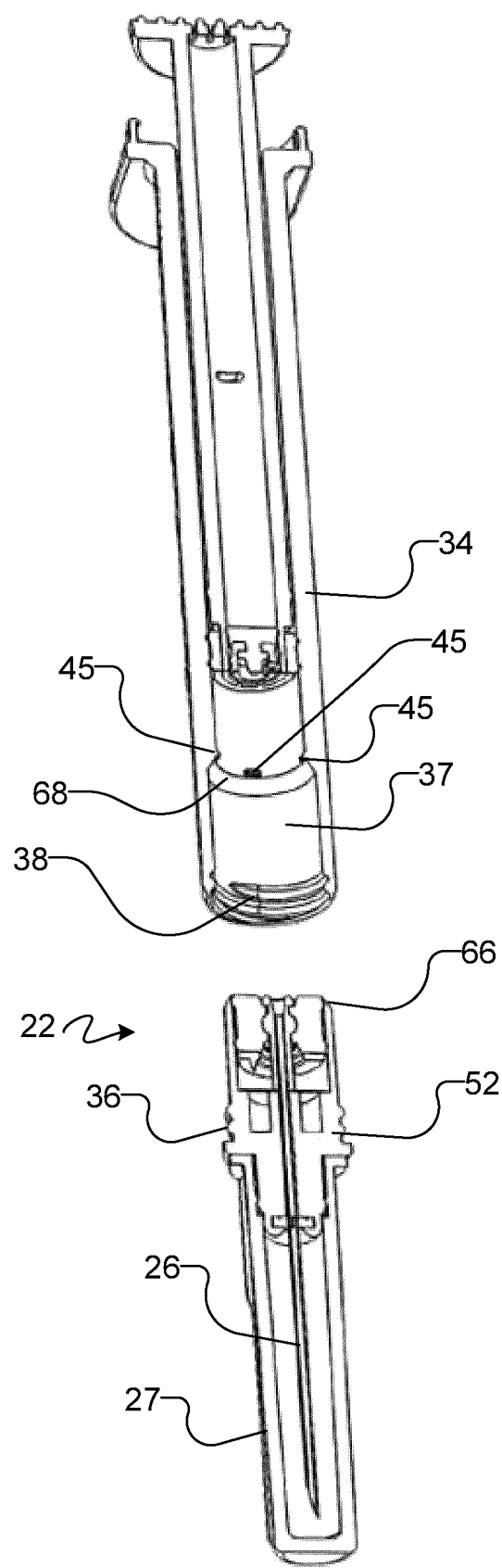
FIG. 3B is a fully cross-sectional view of the embodiment illustrated in FIG. 3A.

FIGS. 3A and 3B show in more detail how modular needle assembly 22 is engageable with syringe body 34. In the illustrated embodiment, threads 36 on needle assembly 22 are engageable with recessed grooves 38 that act as a correspondingly threaded surface on syringe body 34. Any suitable means of engaging modular needle assembly 22 with syringe body 34 could be used, for example a sufficiently tight press or friction fit, snap-fit engagement members, or the like. In some embodiments, the engagement between modular needle assembly 22 and syringe body 34 is reversible, i.e. after modular needle assembly 22 has been engaged with syringe body 34, a user can uncouple modular needle assembly 22 from syringe body 34. In some embodiments, the engagement between modular needle assembly 22 and syringe body 34 is irreversible, i.e. after modular needle assembly 22 has been coupled to syringe body 34, modular needle assembly 22 cannot be removed.

Figure 4:
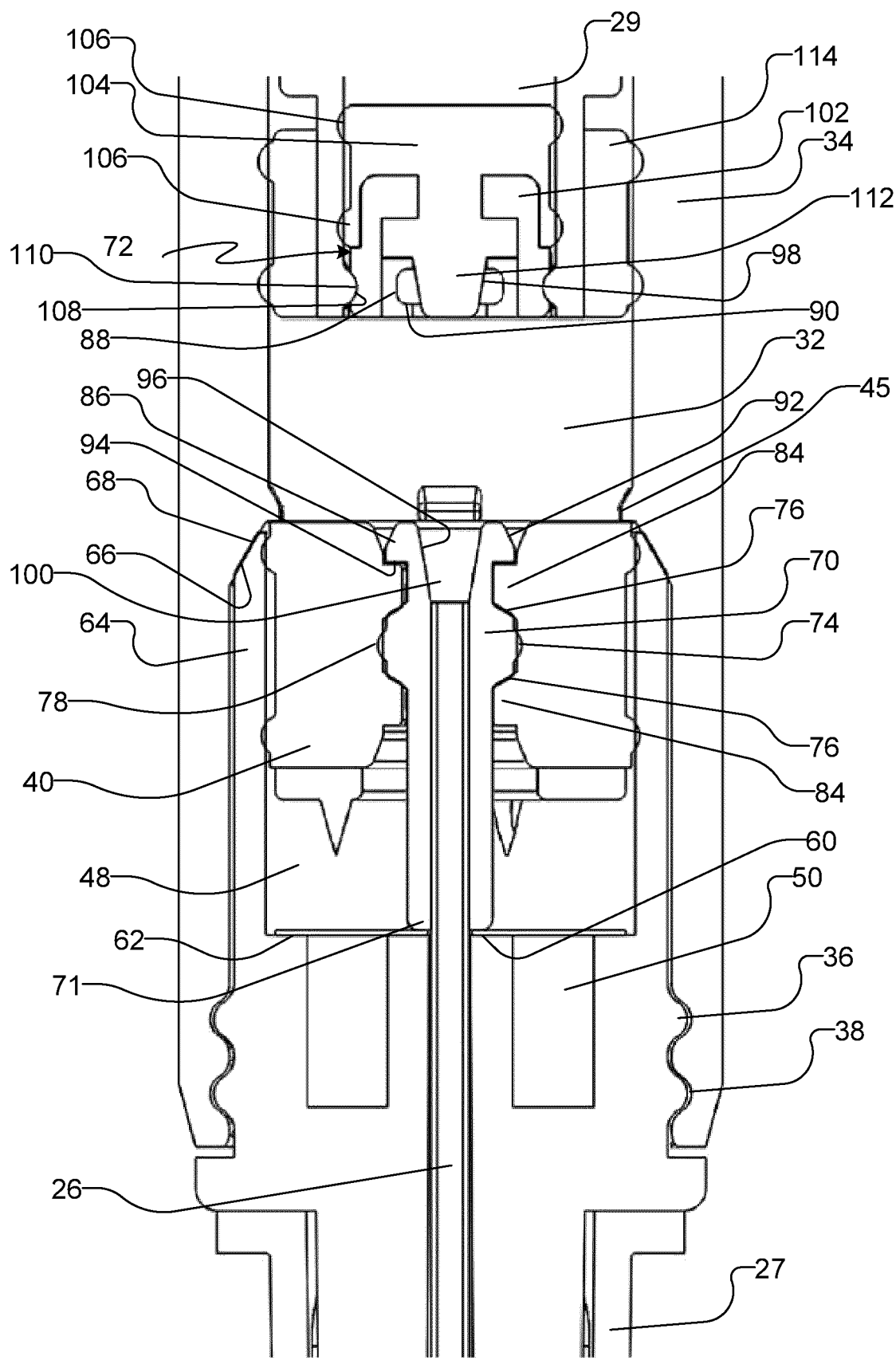
FIG. 4 is a partial cross-sectional view of the modular needle assembly of the example embodiment of FIG. 1, with the needle secured in its initial position.

With reference to FIG. 4, the engagement of needle 26 within modular needle assembly 22 is shown in more detail. Needle 26 is releasably retained in its initial position via a needle hub 70. Needle hub 70 is provided at or near the proximal end of needle 26. In some embodiments, needle 26 is crimped in, cemented to, or otherwise securely fixed to needle hub 70. In some embodiments, needle 22 is insert molded with needle hub 70 to create a single part. Needle hub 70 securely retains needle 26 in place against an injection force or a loading force, but is releasable in the proximal direction in response to the application of a post-injection force applied by a user to retract needle 26.

Needle hub 70 is engageable with grasping features on plunger 28 to provide an assembly for retracting needle 26. In the illustrated embodiment, a locking tip 72 of plunger 28 provides a grasping feature that can engage with needle hub 70 to form a retraction assembly (illustrated as 154 in FIG. 9). Needle hub 70 is also sealingly engageable with false wall 40, to initially secure needle hub 70 (and thus needle 26) in place within modular needle assembly 22.

While the needle hub and locking tip of the embodiment illustrated in FIG. 4 is generally similar to that shown and described in Patent Cooperation Treaty patent application No. PCT/CA2015/051113, which is incorporated by reference herein, any suitable mechanism for engaging and retracting a pneumatically actuated retractable needle can be used, for example, that shown and described in Patent Cooperation Treaty patent application publication Nos. WO 2006/024172 and WO 2012/162821, each of which is incorporated by reference herein.

In the illustrated embodiment, needle hub 70 is initially secured in position by sealing features provided on the outside surface of needle hub 70 that engage with corresponding features provided on the inside surface of a central aperture 39 (FIG. 2) that extends through false wall 40. Needle hub 70 is also supported against movement in the distal direction by contact between a distal end 71 of needle hub 70 with upper proximal edge 60 of inside wall 54, as best shown in FIG. 4. Contact between distal end 71 of needle hub 70 with upper proximal edge 60 as aforesaid prevents needle hub 70 from moving in the distal direction at all times, even upon the application of a post-injection force by a user.

Needle hub 70 has an O-ring seal 74 and two tapered seals 76. O-ring seal 74 is provided as a sealing rib integrally formed with needle hub 70, and sealingly engages with a recess 78 formed on the inside surface of false wall 40.

The tapered seals 76 of needle hub 70 engage respectively with correspondingly shaped tapered regions 80 (FIG. 2) of false wall 40 to provide an additional seal to help prevent medicament from flowing between needle hub 70 and false wall 40. All of false wall 40, O-ring seal 74 and tapered seals 76 are concentric, so that O-ring seal 74 and tapered seals 76 sealingly engage about their full circumferences with recess 78 of false wall 40.

A pair of restraining projections 84 project radially inwardly from the inside surface of false wall 40 proximally and distally of tapered regions 80. The engagement of O-ring seal 74 and tapered seals 76 of needle hub 70 with recess 78 and correspondingly tapered regions 80 of false wall 40 between restraining projections 84 restrains movement of needle hub 70 relative to false wall 40 in the axial direction during the application of a loading force or an injection force.

False wall 40 is frictionally but slidably engaged with the interior surface of perimeter wall 64 of modular needle assembly 22. False wall 40 is axially slidable in response to the application of a post-injection force, but is retained in place by frictional force during the application of a loading or injection force. False wall 40 could be secured in place in any suitable manner that is sufficiently strong to retain false wall 40 in place during the application of a loading or injection force, but releasable in response to the application of a post-injection force. For example, false wall 40 can be initially held in place by frangible members, or weakly secured with adhesive.

In the illustrated embodiment, a plurality of false wall retention features 45 (FIG. 3B) are provided on the interior surface of syringe barrel body 34, to further prevent false wall 40 from being slid in the proximal direction inside syringe barrel body 34, for example when needle 26 is inserted into a patient. In the illustrated embodiment, the false wall retention features comprise one or more radially inwardly extending projections 45 provided on the inside surface of syringe barrel body 34. Radially inwardly extending projections 45 are provided within syringe barrel body 34 at an axial location just proximal of where the proximal portion of perimeter wall 64 of modular needle assembly 22 contacts syringe barrel body 34 when modular needle assembly 22 is in the installed configuration.

In the illustrated embodiment, false wall 40 is provided with a pair of radially outwardly projecting O-ring features 82 (FIG. 2) on its outer surface. O-ring features 82 provide the sealing frictional engagement between false wall 40 and perimeter wall 64. In some embodiments, the use of two O-ring features 82 on false wall 40 assists in ensuring reproducible movement of false wall 40 in response to the application of a post-injection force, by maintaining an appropriate axial alignment of false wall 40 within modular needle assembly 22.

When modular needle assembly 22 is not attached to syringe barrel 30, the friction fit between O-ring features 82 and perimeter wall 64 holds false wall 40, needle hub 70, and needle 26 in position, so that these structures are not moved within body 52 of modular needle assembly 22, for example by ordinary jostling or movement as might occur during the shipping and storage of modular needle assemblies 22. In some embodiments, a friction fit between needle 26 and needle seal 118 (FIG. 2) can also help to retain needle 26 in position in modular needle assembly 22. When a cap 27 is affixed to needle 26 as described below, the cap 27 can assist in ensuring that false wall 40 does not move within the body 52 of modular needle assembly, by preventing forces from being applied against needle 26. In alternative embodiments, O-ring features 82 are omitted, and the material and construction of false wall 40 are selected to provide an appropriate degree of frictional engagement with perimeter wall 64 to initially retain false wall 40, needle hub 70 and needle 26 in position but still allow false wall 40 to be moved on the application of a post-injection force.

In the illustrated embodiment, false wall 40 is provided with a recessed central region 41 (FIG. 2) at its proximal portion. Recessed central region 41 extends distally around central aperture 39 of false wall 40, and receives the generally cylindrical locking element 86 of needle hub 70 described below. Recessed central region 41 allows locking tip 72 to move past and engage with the generally cylindrical locking element 86 (described below) to form a retraction assembly to retract needle 26, without interference by false wall 40.

In the illustrated embodiment, false wall 40 is symmetrical about a central radial axis. Thus, false wall 40 is provided with two recessed central portions 41, one at its distal end and one at its proximal end, even though only one of these recesses receives the generally cylindrical locking element 86 of needle hub 70. In some embodiments, providing a false wall 40 that is symmetrical about a central radial axis avoids a need to ensure that false wall 40 is inserted with a particular orientation during manufacture of modular needle assembly 22.

In the illustrated embodiment, the central aperture 39 of false wall 40 is provided with surface features to prevent the formation of an airtight seal between false wall 40 and needle hub 70 after needle hub 70 has been displaced from its initial position by the release of propellant from unitary propellant release structure 24. This ensures that a passageway is available for the flow of propellant from unitary propellant release structure 24 after seal 44 has been ruptured to retract needle 26. In the illustrated embodiment, the surface features that prevent formation of an airtight seal are channels 43 (FIG. 2). Channels 43 extend axially along projections 84 of false wall 40 to provide a passageway for the flow of propellant between needle hub 70 and false wall 40 after needle hub 70 has been initially dislodged from false wall 40 (and the seals provided by O-ring seal 74 and tapered seals 76 have thereby been removed) by the application of a post-injection force by a user, to ensure propellant can flow and force the needle retraction assembly 154 in the proximal direction.

In the illustrated embodiment, the structure of false wall 40 also helps to ensure that no seal is formed between false wall 40 and inside wall 54. For example, if false wall 40 had a recessed central portion 41 only at the proximal end thereof, there would be a risk that a seal could be formed between the distal edge of false wall 40 and upper proximal edge 60 of inside wall 54. In such embodiments, alternative structures, such as appropriately located channels within false wall 40 or extensions of channels 43 could be provided to minimize the risk that a seal would be formed between false wall 40 and both upper proximal edges 60, 62 of inside wall 54 and outside wall 56, which could thereby contain propellant within channel 50 instead of allowing propellant to be released into upper chamber 48 of modular needle assembly 22 to retract needle retraction assembly 154. In the illustrated embodiment, the tapered inside diameter provided at the distal portion of false wall 40 prevents a seal from being formed between false wall 40 and inside wall 54. In some embodiments, the tapered inside diameter provided at the distal portion of false wall 40 could be different from the tapered inside diameter provided as recess 41 for receiving generally cylindrical locking element 86 of needle hub 70, i.e. false wall 40 need not be symmetrical about a central radial axis.

In the illustrated embodiment, the proximal portion of needle hub 70 sits flush with the proximal portion of false wall 40. In some embodiments, this configuration helps to minimize the dead volume within retractable needle syringe 20, and also minimizes the risk that needle hub 70 may be bumped or moved during shipping, storage, or assembly onto syringe body 34. However, other configurations could be used, for example, the proximal end of needle hub 70 could project slightly in the proximal direction from false wall 40, or could be slightly recessed within false wall 40, as long as a corresponding recess is provided within false wall 40 to allow needle hub 70 to engage with locking tip 72, as described below.

Locking tip 72 is positioned and configured to be engageable with needle hub 70 to form a retraction assembly for retracting needle 26. In some embodiments, locking tip 72 is also positioned and configured to sealingly engage with needle hub 70, to prevent any further flow of medicament and/or bodily fluids through needle 26.

Needle hub 70 is provided with corresponding features for engaging with locking tip 72 to provide a retraction assembly for retracting needle 26. In some embodiments, needle hub 70 is also provided with corresponding features to sealingly engage with locking tip 72.

In the illustrated embodiment, needle hub 70 is provided with snap features to engage in a snap-fit engagement with locking tip 72. In the illustrated embodiment, the snap features of needle hub 70 comprise a generally cylindrical locking element 86 at the proximal end of needle hub 70 that is positioned to engage with a locking channel 88 and locking edge 90 (FIG. 4) provided on locking tip 72. The generally cylindrical locking element 86 of needle hub 70 has an outer tapered portion 92 and a radially extending locking edge 94. Outer tapered portion 92 flares radially outwardly in the distal direction from the proximal end of needle hub 70, to provide locking edge 94 along the outside distal edge portion thereof. In use, outer tapered portion 92 can slide inside locking tip 72 of plunger 28, to allow locking edge 94 to slide past and then engage in snap-fit engagement with locking channel 88, as described below.

Although the outer tapered portion 92 and locking edge 94 of generally cylindrical locking element 86 of needle hub 70 have been described and illustrated as generally circular, it is alternatively possible for these elements to be provided as one or more discrete projections positioned to be engageable by locking channel 88 in use (i.e. generally cylindrical locking element 86 could be broken into one or more discontinuous pieces, rather than being one fully revolved element). In some embodiments, providing the locking element of needle hub 70 as a generally cylindrical locking element eliminates a need to ensure that needle hub 70 is placed in a specific orientation during the manufacture of modular needle assembly 22 (i.e. so that locking element 86 will be available for engagement with locking channel 88 no matter what orientation it is inserted at within false wall 40).

In some embodiments, including the illustrated embodiment, needle hub 70 also includes sealing features for sealingly engaging with locking tip 72. In the illustrated embodiment, the sealing feature of needle hub 70 is provided by an inner tapered surface 96 that engages with a correspondingly tapered surface 98 provided on locking tip 72. Inner tapered surface 96 is provided in the proximal portion of needle hub 70, which is generally cylindrical with an axially extending opening 100 therethrough, so that fluid can flow through needle 26 into and out of medicament chamber 32. Inner tapered surface 96 tapers inwardly in the distal direction, so that tapered surface 96 tapers inwardly towards the proximal portion of needle 28. The proximal portion of opening 100 is thus wider than the distal portion of opening 100, so that tapered surface 98 of locking tip 72 can be received therein in sealing engagement.

In the illustrated embodiment, locking tip 72 is made as a single part with two components as an overmold: a rigid component 102 and a more flexible overmolded component 104, to enhance manufacturing convenience and provide a reduction in manufacturing cost. Rigid component 102 includes locking channel 88 for engaging with needle hub 70 in a snap-fit engagement. Rigid component 102 also engages locking tip 72 in place at the distal tip of plunger 28. Overmolded component 104 sealingly engages with the interior surface of retraction lumen 29, to prevent medicament from flowing past locking tip 72 and to ensure a good seal so that pressure can be applied by released propellant to move the needle retraction assembly in the proximal direction during needle retraction. Suitable examples of material for the manufacture of rigid component 102 include a rigid material such as rigid plastic like polycarbonate, Styrolux™, polypropylene, or the like. Suitable examples of material for the manufacture of overmolded component 104 include relatively more flexible materials such as silicone, thermoplastic elastomer or other similar polymer, or the like.

Rigid component 102 of locking tip 72 has a generally cylindrical shape so that it can fit within plunger lumen 29, and includes at least one locking channel 88 formed on a distal edge thereof, for engaging in snap-fit engagement with locking edge 94 of needle hub 70 via locking edge 90. While in the illustrated embodiment, locking channel 88 is shown as extending through a portion of rigid component 102, any suitable configuration that allows for snap-fit engagement with locking edge 94 of needle hub 70 could be used. For example, two, three, or more locking apertures could be provided for engagement with locking edge 94. Additionally, while locking channel 88 has been shown as being formed as a slot or aperture through rigid component 102, locking channel 88 could alternatively be formed as a channel on the inside surface of rigid component 102, without extending fully therethrough.

Overmolded component 104 of locking tip 72 has a pair of sealing rings 106 that are provided by radially outwardly extending protrusions on the outside circumference of overmolded component 104. Different numbers of sealing rings, or a continuous sealing surface, could be used. In some embodiments, the use of two sealing rings rather than just one sealing ring can help to ensure the linear travel of the needle retraction assembly during retraction. Sealing rings 106 are sealingly engaged with the inside surface of retraction lumen 29.

Rigid component 102 of locking tip 72 also includes distal grooves 108 that engage with capture projections 110 on the inside surface of the distal end of plunger 28, to secure locking tip 72 to plunger 28 prior to needle retraction. Distal groove 108 extends radially inwardly around a distal portion of the outside surface of locking tip 72. Capture projections 110 extend radially inwardly from the inside surface of the distal end of plunger 28.

In alternative embodiments, capture projections 110 and/or distal groove 108 could be omitted, and a different engagement between locking tip 72 and the distal end of plunger 28 could be used, for example, a sufficiently tight but releasable press or friction fit, connection by easily frangible connectors or a breakable piece of material that prevents locking tip 72 from releasing during the application of a loading or injection force but allows release of locking tip 72 in response to a post-injection force, or the like.

The engagement of distal grooves 108 and capture projections 110, aided by the sealing engagement between sealing rings 106 and retraction lumen 29 is sufficiently strong that locking tip 72 does not move relative to plunger 28 in response to the application of a loading force or an injection force, but also such that the engagement between distal grooves 108 and capture projections 110 is broken by the application of a post-injection force, and sealing rings 106 permit locking tip 72 (and hence the needle retraction assembly) to slideably move within retraction lumen 29 in response to pressure applied by released propellant after the rupture of seal 44.

Overmolded component 104 of locking tip 72 also includes a central cylindrical projection 112, with a tapered surface 98 that is complementary to inner tapered surface 96 of needle hub 70 (i.e. tapered surface 98 is tapered inwardly from its proximal end to its distal end), so that engagement of tapered surfaces 96, 98 when a user applies a post-injection force provides a seal to prevent any further fluid flow through needle 26. Central cylindrical projection 112 is positioned at the distal portion of overmolded component 104, and sits within and is axially aligned with rigid component 102 so that it can engage with needle hub 70.

To facilitate injection of medicament, the distal tip of plunger 28 is also provided with a plunger seal 114. In the illustrated embodiment, plunger seal 114 is manufactured as an overmold to plunger 28. In such embodiments, plunger seal 114 is an elastomeric overmold. In other embodiments, plunger seal 114 is manufactured as a separate part from plunger 28 and the two elements are joined together in any suitable manner, for example by a sufficiently tight friction fit, use of suitable adhesives, engagement of a projection on plunger seal 114 within a corresponding groove formed on the outer surface of the distal tip of plunger 28, or the like. Plunger seal 114 surrounds the outside portion of the distal tip of plunger 28, and sealingly but slidingly engages the interior surface of syringe body 34 to facilitate injection of medicament in a similar manner to conventional syringes.

Needle 26 is hollow and has a downstream tip 116 (FIG. 1) for injection of medicament into a subject and an upstream intake opening for receiving medicament from medicament chamber 32. In some embodiments, a needle seal 118 (FIG. 2) is provided to seal the distal end of modular needle assembly 22. In some embodiments, needle seal 118 is secured to modular needle assembly 22 in any suitable manner, for example by suitable adhesives, by compression fit between portions of modular needle assembly 22, overmolding, or the like. Needle seal 118 is made from any suitable material, for example a soft, flexible material such as silicon or rubber, including polyisoprene. In the illustrated embodiment, needle seal 118 is held in place by a sealing projection 119, provided on the portion of the body 52 of modular needle assembly 22 that contacts needle seal 118. During assembly of modular needle assembly 22, needle seal 118 can be swaged in place within body 52, and is compressed against sealing projection 119 to prevent leakage of fluids or gases past the outer diameter of needle seal 118.

Figure 7:
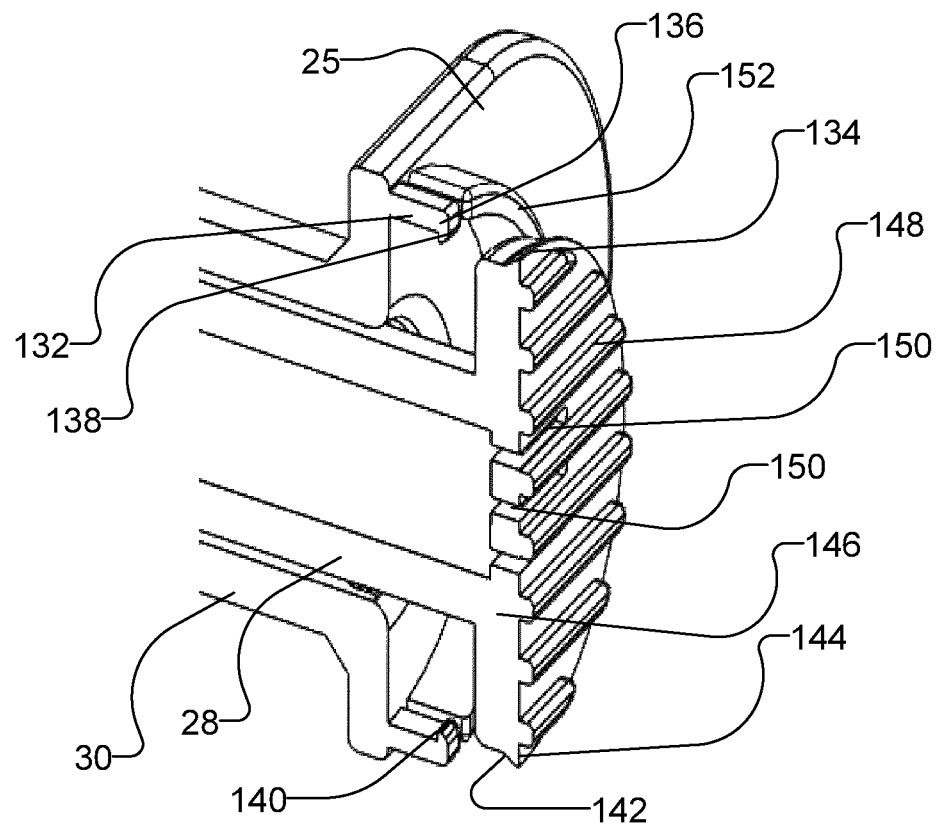
FIG. 7 is a partial cross-sectional view the embodiment of FIG. 1 showing the engagement between the plunger and the syringe barrel.

In some embodiments, plunger 28 includes one or more passageways, such as vent holes 120, formed therethrough. In some embodiments, vent holes 120 allow release of air from retraction lumen 29 upstream of the needle retraction assembly 154 when needle 26 is retracted. In some embodiments, vent holes 120 are positioned in a sidewall of plunger 28 proximally at or close to the upstream limit of travel of the needle retraction assembly when fully retracted, to avoid a loss of propellant pressure (and resultant upstream biasing force) that could stop the upstream travel of needle 26 before it has been fully retracted as could occur if, for example, vent holes 120 are positioned too far distally of the upstream limit of travel of the needle retraction assembly. In some embodiments, vent holes 120 are positioned a sufficient distance proximally of locking tip 72 that the total combined length of the needle retraction assembly can be received within the syringe barrel distally of vent holes 120, so that no part of needle 26 projects outside of modular needle assembly 22. Once locking tip 72 moves proximally past the vent holes, a passageway is opened between upper chamber 48 and the external atmosphere via the gap between plunger 28 and syringe barrel 30, so that any excess propellant is released to the atmosphere after needle 26 has been retracted. In some embodiments, as illustrated in FIG. 7, vent holes 150 are provided through the proximal wall of plunger 28 in addition to and/or as an alternative to vent holes in a sidewall of plunger 28, such as vent hole 120.

Figure 5:
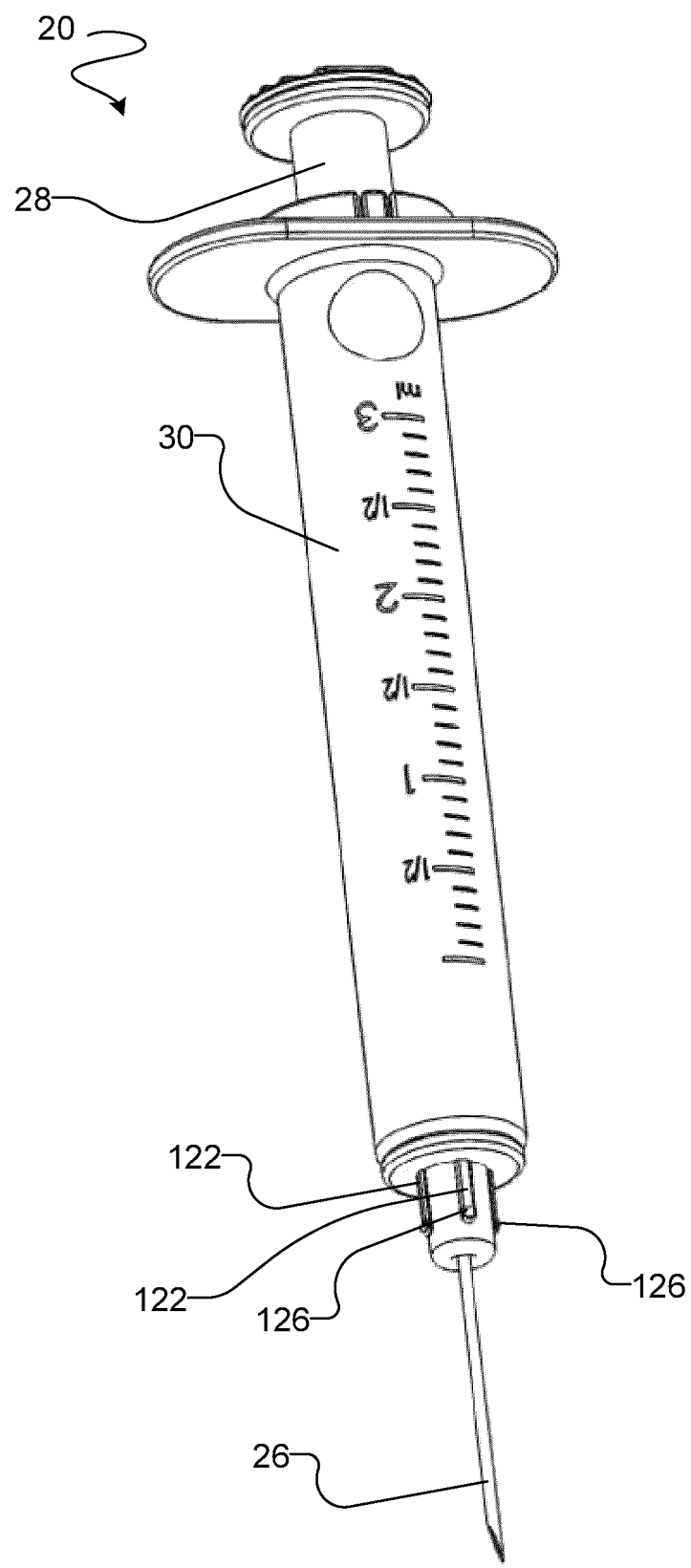
FIG. 5 is a perspective view of a modular needle assembly of one example embodiment secured on the body of a syringe.

As illustrated in FIG. 5, in some embodiments, structural features are provided to assist a user in twisting modular needle assembly 22 to secure it to syringe body 34. In the illustrated embodiment, engagement projections are provided on the outside surface of modular needle assembly 22, which can be used to secure modular needle assembly 22 against rotational movement within cap 27. Cap 27 is provided with corresponding recesses for receiving the engagement projections to provide this function.

Figure 6:
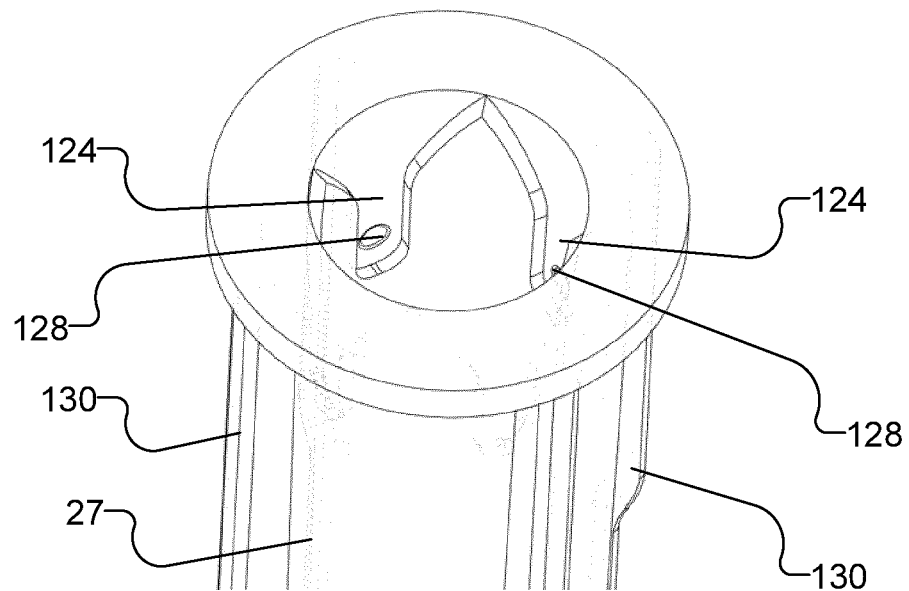
FIG. 6 is a partial perspective view showing an example embodiment of a cap for capping the needle of the modular needle assembly of the example embodiment of FIG. 5.

In the illustrated embodiment, a plurality of radially outwardly projecting alignment tabs 122 are provided on the outside circumference of the body 52 of modular needle assembly 22, and are positioned and configured to align with corresponding recessed channels 124 (FIG. 6) formed at the proximal end of the inside surface of cap 27. The sliding engagement of alignment tabs 122 and recessed channels 124 guides cap 27 to the secured position. To secure cap 27 in the secured position, the illustrated embodiment also includes a plurality of radially outwardly extending snap projections 126 (positioned one on each of the alignment tabs 122 in the illustrated embodiment), that are engageable with a plurality of corresponding snap depressions 128 formed on the inside of cap 27. The described example embodiment is just one way that cap 27 can be secured to modular needle assembly 22 to cover needle 26, and any suitable needle cover can be used for this purpose. For example, in some embodiments, cap 27 may be laminated, cemented, snapped, press fit, or otherwise removably affixed in any other manner to modular needle assembly 22.

In the illustrated embodiment, cap 27 further includes a plurality of radially outwardly extending ribs 130, which can be grasped by a user to assist in applying rotational force to modular needle assembly 22 when securing modular needle assembly 22 on syringe body 34. In use, cap 27 can be twisted or snapped off, or otherwise removed in any suitable manner, to expose needle 26 for use.

In some embodiments, structural features are provided to lock plunger 28 at or near its downstream limit of travel after syringe 20 has been used, for example to prevent re-use of needle 26 or to provide the used retractable needle syringe 20 with a more compact profile. Any suitable structural features can be used for this purpose, for example an inwardly extending flange projection from syringe barrel 30 that is engageable with an outwardly projecting plunger lock verge provided on the outer circumference of plunger 28 to permit only relative downstream movement of the plunger as described in U.S. Pat. No. 7,811,259; or a snap-fit plunger locking mechanism as illustrated in FIG. 7. In such an embodiment, a pair of snap-fit engagement members 132, 134 are positioned at the proximal end of each of syringe barrel 30 and plunger 28. In the illustrated embodiment, a syringe snap-fit engagement member 132 provided at the proximal end of syringe barrel 30 projects in the proximal direction from the proximal end of syringe barrel 30, and has a radially inwardly extending locking projection 136 at its proximal end. Locking projection 136 has an inwardly angled sliding surface 138 past which a corresponding angled sliding surface 142 of plunger 28 can slide (inwardly angled sliding surface 138 is angled inwardly and distally relative to the outside edge of locking projection 136), and a radially extending locking surface 140 located distally of sliding surface 138. Locking surface 140 is configured to lock with corresponding locking surface 144 of plunger 28. In the illustrated embodiment, locking surface 140 extends generally straight in the radial direction and locking surface 144 likewise extends generally straight in the radial direction, so that once locking surface 144 slides past angled sliding surface 138 and engages with locking surface 140, plunger 28 cannot thereafter be withdrawn from syringe barrel 30.

Plunger snap-fit engagement member 134 has an outwardly angled sliding surface 142 that can slide past inwardly angled sliding surface 138, and a generally radially extending locking surface 144 that can slide past and engage with locking surface 140. Angled sliding surface 142 has a shape that is complementary to angled sliding surface 138 (angled outwardly and proximally relative to the proximal end of plunger 28 in the illustrated embodiment), and alternative complementary shapes that can slide past one another, e.g. slightly curved surfaces, could be used for surfaces 138, 142 in alternative embodiments. In use, at or just before the end of the application of a post-injection force, a user will cause angled sliding surfaces 138, 142 to move past one another, allowing locking surfaces 140, 144 to come into contact in a snap-fit engagement, thereby locking plunger 28 within syringe barrel 30.

In the illustrated embodiment, two pairs of snap-fit engagement members 132, 134 are provided, one on each opposing side of syringe assembly 20. Any desired number and location of snap-fit engagement members 132, 134 could be used (e.g. three, four or more pairs of snap-fit engagement members 132, 134), so long as these can be used to lock plunger 28 within syringe barrel 30.

In some embodiments, plunger 28 includes a plunger end flange 146 to provide a bearing surface for the fingers of a user to push and pull against to load and inject medicament into/out of medicament chamber 32 or apply a post-injection force. In some embodiments, plunger 28 includes a plurality of thumb ridges 148 on the distal portion of plunger 28 and/or on plunger end flange 146. In some embodiments, thumb ridges 148 prevent a user's fingers from occluding vents 150 provided at the distal end of plunger 28 in some embodiments.

In some embodiments, including the embodiment illustrated in FIG. 7, a generally circular anti-tamper ring 152 is provided that is shaped and positioned to receive therein the correspondingly shaped proximal end of plunger 28. Anti-tamper ring 152 projects axially in the proximal direction from the proximal end of syringe body 34, so that when snap-fit engagement members 132, 134 are locked together, anti-tamper ring 152 encircles the proximal end of plunger 28. While a generally circular shape is described and illustrated, other corresponding shapes could be used, so long as anti-tamper ring 152 generally surrounds the distal end of plunger 28 and prevents a user from inserting tools to pull plunger 28 out of syringe barrel body 34.

In use, a user selects a modular needle assembly 22 and a syringe barrel 30 having a desired volume. The user couples modular needle assembly 22 to syringe barrel 30 by inserting perimeter wall 64 inside the distal cavity 37 of syringe barrel 30 and engaging threads 36 of needle assembly 22 with threaded grooves 38 of syringe body 34 by applying a relative twisting motion. A user then removes cap 27 from needle 26 and draws medicament into medicament chamber 32 in the same manner as for an ordinary hypodermic needle syringe, applying a loading force to plunger 28 in the proximal direction. A user then expels undesired air from medicament chamber 32, for example by inverting the syringe so that needle 26 extends generally vertically upwards, tapping the side of syringe body 34 to displace any air bubbles lodged within medicament chamber 32 vertically upwards, and depressing plunger 28 slightly to force air out of needle 26. The medicament is thus ready for injection into a subject.

To administer the medicament, needle 26 is inserted through the skin of a subject, and plunger 28 is depressed in the conventional manner by the application of an injection force in the distal direction to force medicament out of needle 26 and into the subject. Needle 26 is then withdrawn from the subject, although needle 26 can be optionally left in the subject while the retraction process is carried out.

Figure 8:
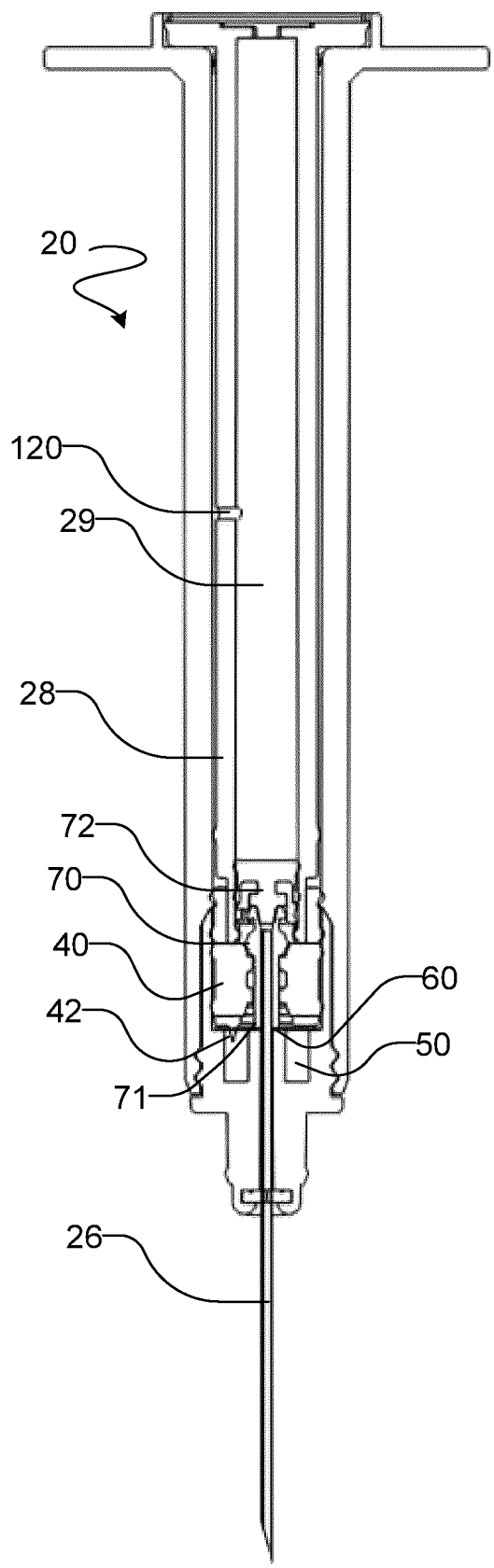
FIG. 8 is a cross-sectional view of the embodiment of FIG. 1 after a user has applied a post-injection force to the device to engage the locking tip with the needle hub and rupture the seal covering the unitary propellant release structure.

To retract needle 26, a user continues to apply force against plunger 28 in the distal direction. This force is now a post-injection force. In some embodiments, the post-injection force required to retract needle 26 is greater than the injection force required to inject medicament into a patient. Continued application of the post-injection force moves the distal tip of plunger 28 and plunger seal 114 distally over false wall retention features 45, causing the distal tip of plunger 28 to impinge on and apply a force in the distal direction on false wall 40. The configuration of retractable needle syringe 20 after the application of a post-injection force by a user is shown in FIG. 8.

The engagement of needle hub 70 in false wall 40 is sufficiently strong that needle hub 70 is prevented from relative movement with false wall 40 during the application of an injection force or a loading force by a user, but weak enough that movement of false wall 40 produced by the application of a post-injection force via plunger 20 forces false wall 40 to slide distally past needle hub 70 within upper chamber 48. Needle hub 70 is itself restrained against distal movement via contact of its distal end 71 with the upper proximal edge 60 of inside wall 54, which rigidly resists distal movement of needle hub 70.

Similarly, the engagement of locking tip 72 within the distal tip of plunger 28 is sufficiently strong that locking tip 72 does not move within the distal tip of plunger 28 during the application of a loading force or an injection force. However, this engagement is broken by the application of a post-injection force by a user, so that locking tip 72, needle hub 70, and needle 26 can be retracted within retraction lumen 29 by propellant released from unitary propellant release structure 24, as described below.

When a user applies a post-injection force, needle hub 70 is prevented from moving in the distal direction via the engagement of its distal tip 71 with the upper proximal edge 60 of inside wall 54 of unitary propellant release structure 24. However, false wall 40 is slideable in the distal direction in response to the application of the post-injection force as transmitted through movement of the distal tip of plunger 28 pressing against false wall 40, and upper restraining projection 84 of false wall 40 is forced to slide over tapered seals 76 and O-ring seal 74 of needle hub 70, so that needle hub 70 is released from its engagement with false wall 40.

As the distal tip of plunger 28 continues to move in the distal direction by reason of the application of the post-injection force, central cylindrical projection 112 of locking tip 72 slides into axially extending opening 100 of needle hub 70. Tapered surface 98 of locking tip 72 is thus brought into engagement with inner tapered surface 96 of needle hub 70, to provide a seal that prevents the further flow of medicament or bodily fluids through needle 26. Movement of the distal tip of plunger 28 in the distal direction also causes locking channel 88 of locking tip 72 to slide past outer tapered portion 92 of needle hub 70, so that locking edges 90, 94 are brought into engagement to lock locking tip 72 and needle hub 70 together to provide (together with needle 26) a needle retraction assembly (shown as 154 in FIG. 9).

In the illustrated embodiment, the engagement of distal groove 108 of locking tip 72 and capture projections 110 of plunger 28 is broken by the application of a post-injection force by a user. The force required to disengage distal groove 108 from capture projections 110 should be greater than the force required to engage locking tip 72 with needle hub 70. If the force required to disengage distal groove 108 from capture projections 110 is similar to or less than the force required to sealingly engage locking tip 72 with needle hub 70, then there is a risk that locking tip 72 will disengage from distal groove 108 and be shifted proximally within retraction lumen 29 on the application of a post-injection force by a user, without engaging with needle hub 70. This would result in no retraction of needle 26.

Movement of false wall 40 in the distal direction also causes rupturing members 42 to move in the distal direction. Rupturing members 42 are oriented so that continued movement in the distal direction results in the rupture of seal 44, thereby releasing propellant from unitary propellant release structure 24 into upper chamber 48 of modular needle assembly 22. The propellant is prevented from escaping past the needle retraction assembly 154 by the engagement of sealing rings 106 of locking tip 72 with the inside surface of plunger 28. The propellant is prevented from flowing out through needle 26 by the sealing engagement of tapered surfaces 96, 98 of needle hub 70 and locking tip 72, respectively.

Figure 9:
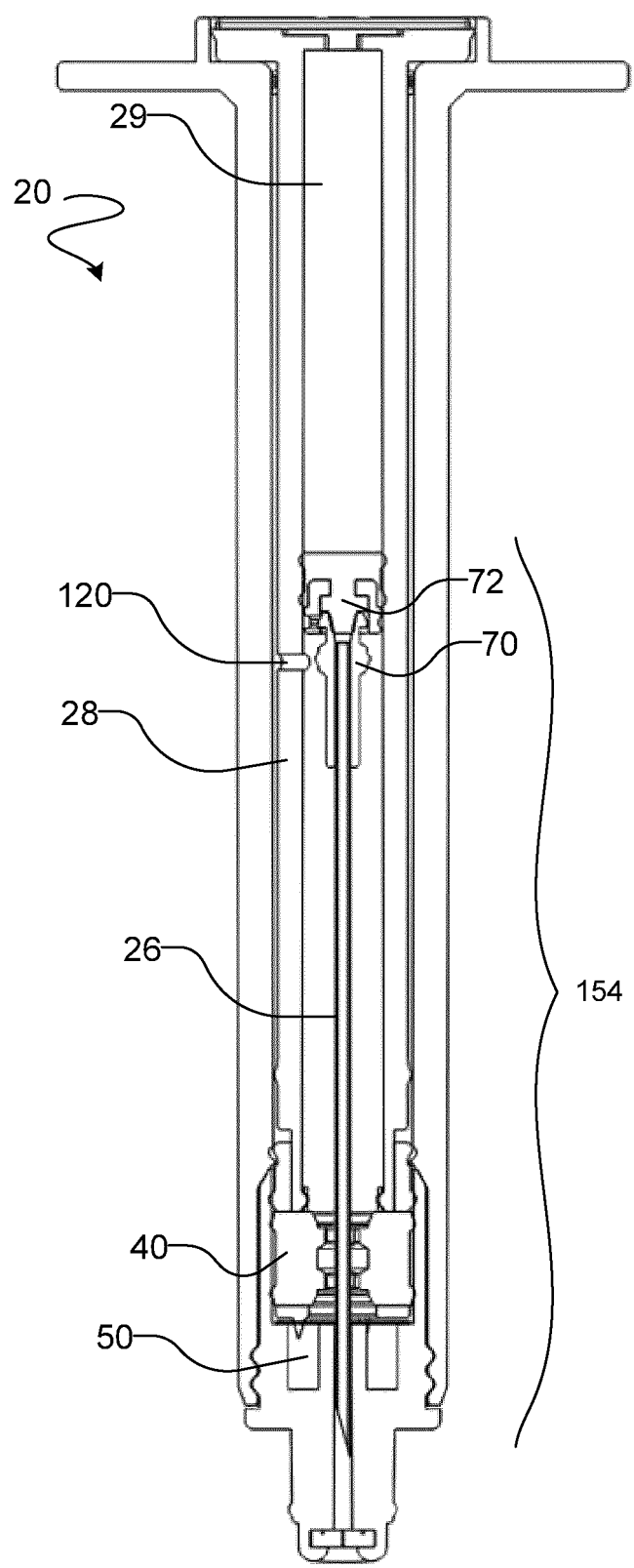
FIG. 9 is a cross-sectional view of the embodiment of FIG. 1 after the needle has been fully retracted.

The released propellant applies a proximal force against the needle retraction assembly 154 (i.e. needle hub 70, locking tip 72, and needle 26), so that needle 26 is retracted. The engagement of sealing rings 106 of locking tip 72 allows the needle retraction assembly 154 to slide within retraction lumen 29 under the influence of the released propellant. A sufficient amount of propellant is provided within unitary propellant release structure 24 so that needle 26 is retracted a distance sufficient that the tip 116 of needle 26 sits fully within syringe body 34 or the body 52 of modular needle assembly 22, so that syringe 20 no longer presents a sharps hazard. Any excess propellant pressure is vented after locking tip 72 passes vent hole 120, and the retraction assembly will come to a rest within retraction lumen 29, as illustrated in FIG. 9.

While unitary propellant release structure 24 has been described above with reference to a generally cylindrical channel 50 formed in modular needle assembly 22 and covered by a seal 44, it will be apparent to those skilled in the art that other configurations could be used to achieve the same function. For example, with reference to FIGS. 10A and 10B, example embodiments in which channel 50 has been provided with irregular shapes are contemplated.

Figure 10A:
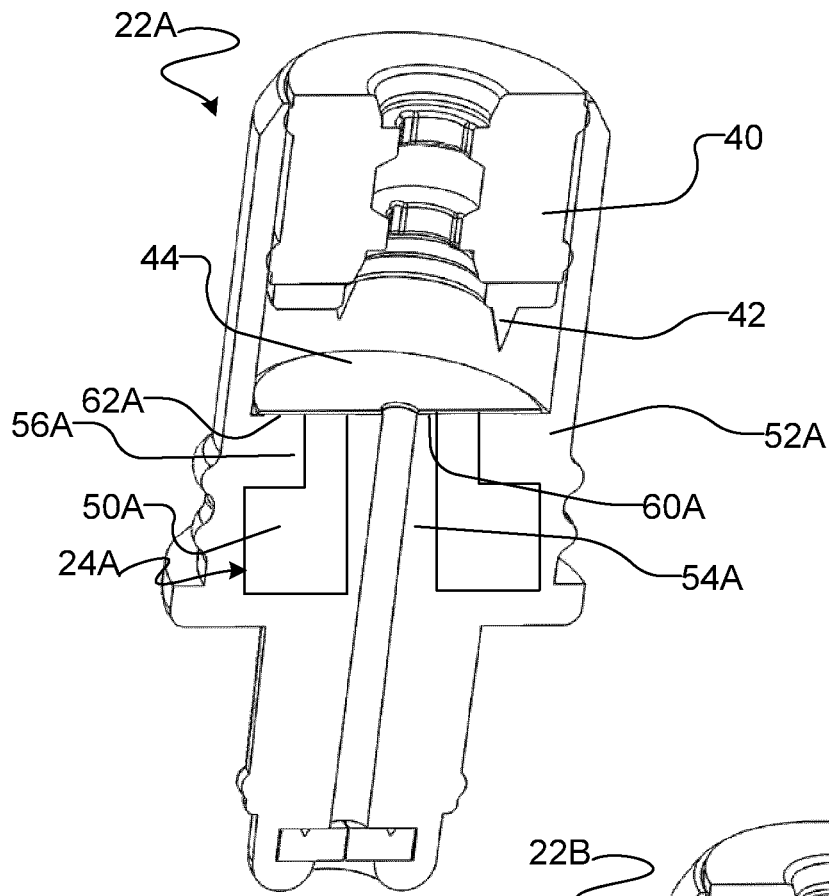
FIGS. 10A and 10B are cross-sectional views of example embodiments of different channel structures that can be used to provide a unitary propellant release structure.

In the example embodiment of a modular needle assembly 22A illustrated in FIG. 10A, channel 50A has been provided with a relatively wide lower portion and a narrower upper portion. Channel 50A is provided with sufficient volume to hold a sufficient amount of propellant to be able to perform retraction of needle 26, and channel 50A is still positioned and configured to allow rupturing members 42 to rupture seal 44 and release propellant from unitary propellant release structure 24A. Upper proximal edge 60A of inside wall 54A and upper proximal edge 62A of outside wall 56A are still provided, so that seal 44 can be sealingly secured in place over channel 50A to contain propellant within unitary propellant release structure 24A.

Figure 10B:
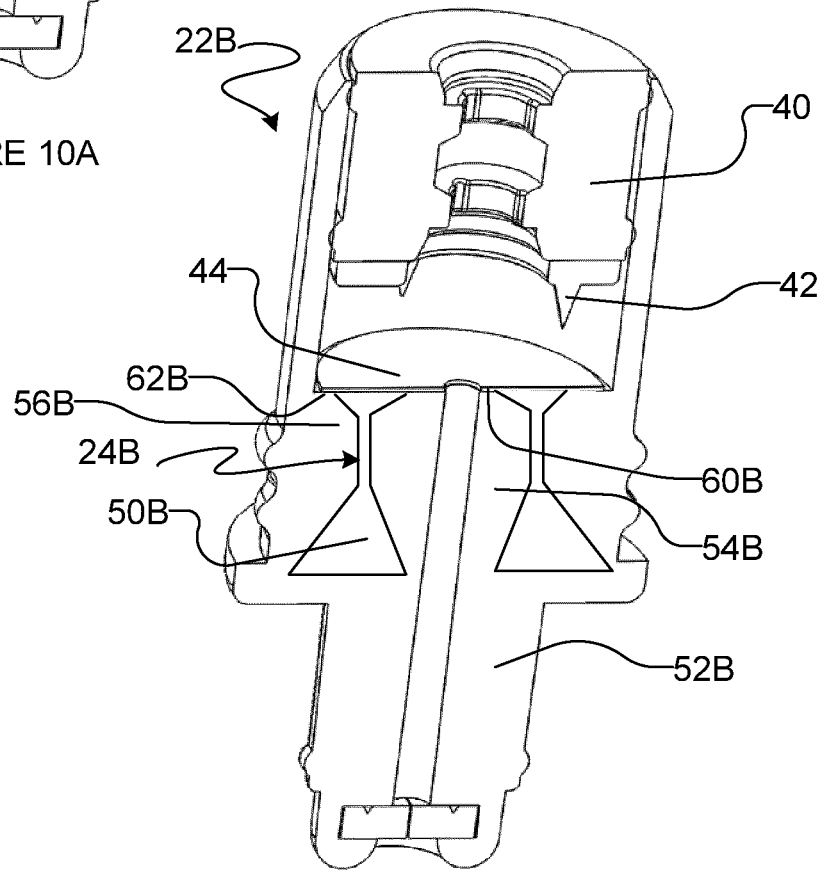

Similarly, in the example embodiment of a modular needle assembly 22B illustrated in FIG. 10B, channel 50B has been provided with a different shape, having a generally triangular upper portion and a generally triangular lower portion connected by a connecting passageway. Again, channel 50B is provided with sufficient volume to hold a sufficient amount of propellant to be able to perform retraction of needle 26, and channel 50B is still positioned and configured to allow rupturing members 42 to rupture seal 44 and release propellant from unitary propellant release structure 24B. Upper proximal edge 60B of inside wall 54B and upper proximal edge 62B of outside wall 56B are still provided, so that seal 44 can be sealingly secured in place over channel 50B to contain propellant within unitary propellant release structure 24B.

Figure 11:
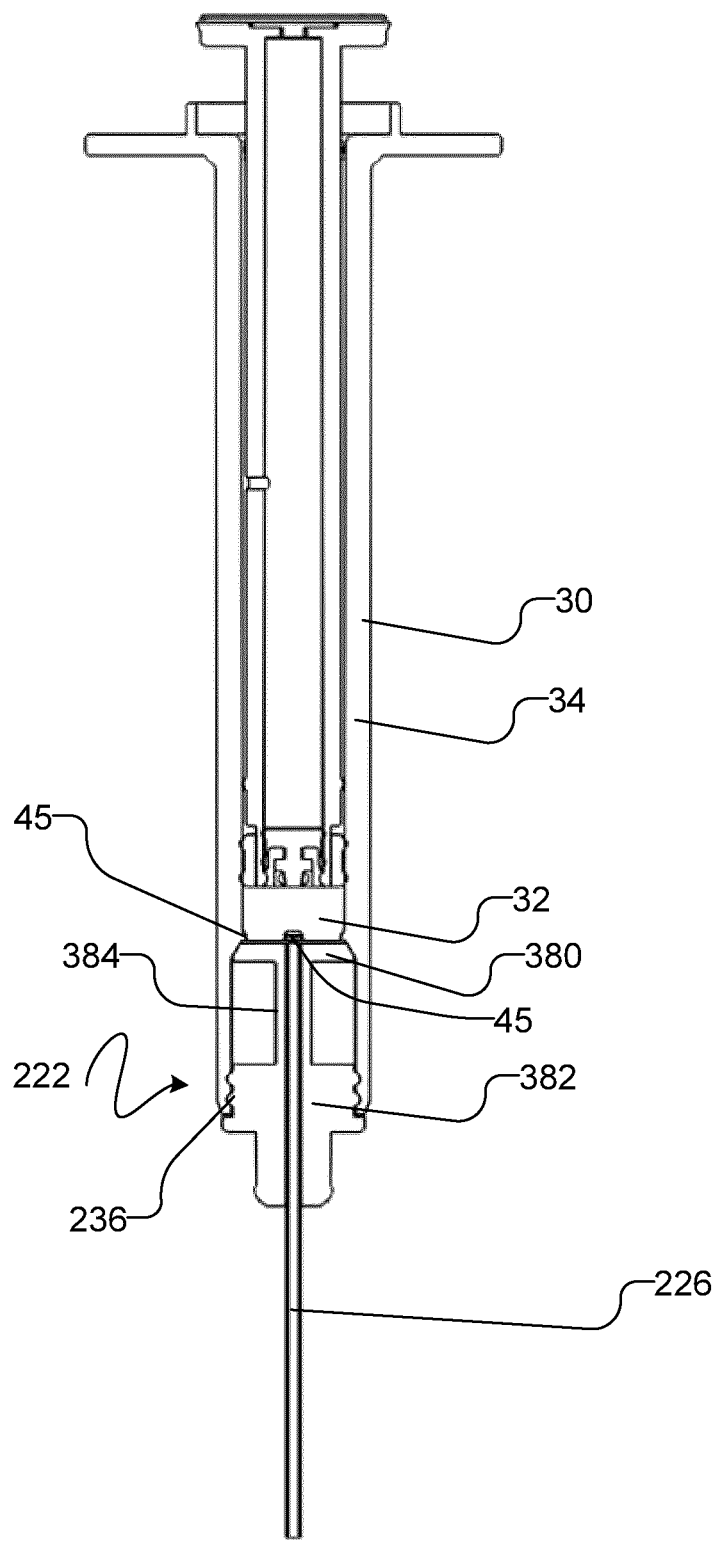
FIG. 11 is a cross-sectional view of an example embodiment of a non-retractable filler needle module coupled to a syringe body.
Figure 12:
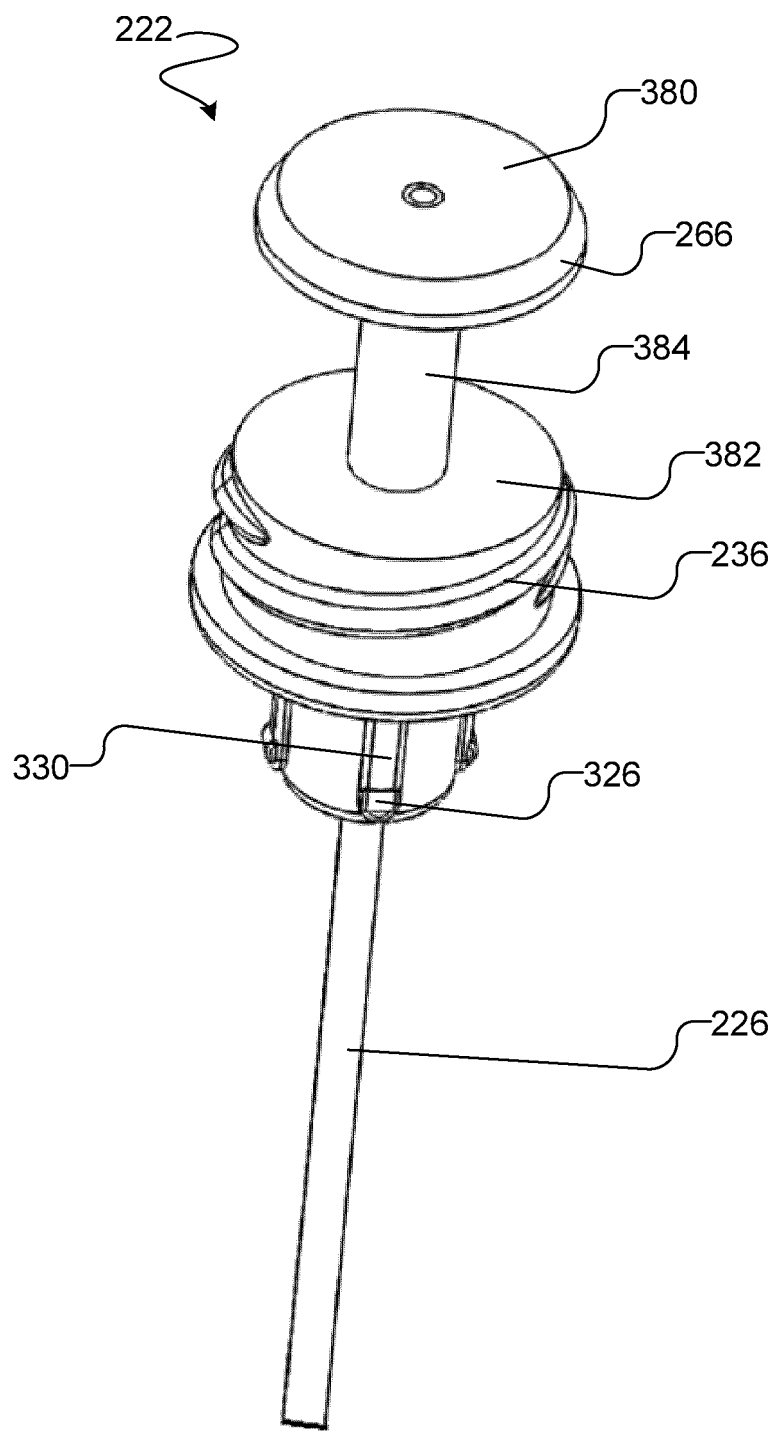
FIG. 12 is a perspective view of an example embodiment of a non-retractable filler needle module.
Figure 13:
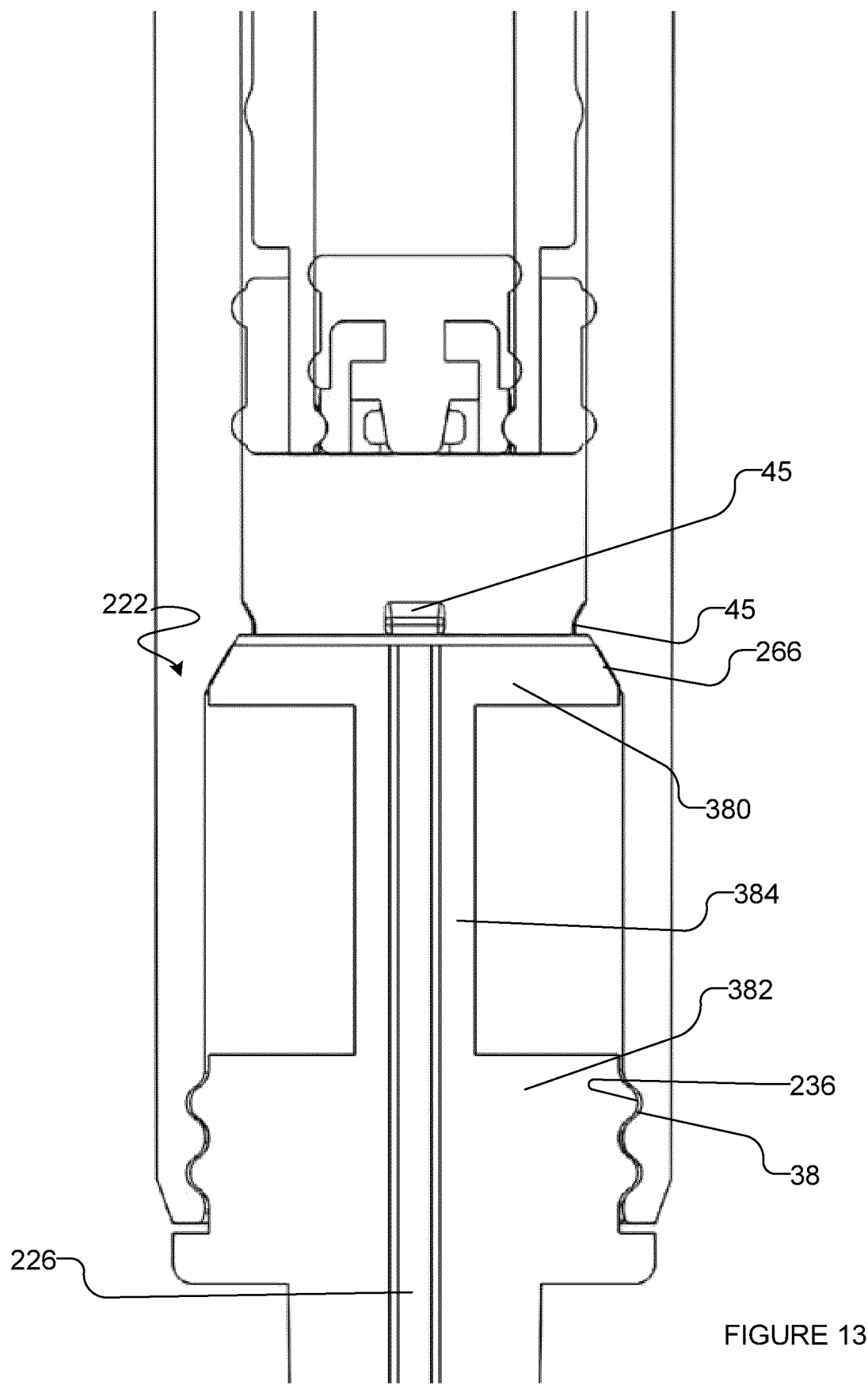
FIG. 13 is a partial cross-sectional view of the example embodiment of a non-retractable filler needle module as shown in FIG. 11 coupled to a syringe body.

In some embodiments, as illustrated in FIGS. 11-13, a modular filler needle assembly 222 is provided that is engageable with syringe barrel 30. Parts of modular filler needle assembly 222 that are similar to those of modular needle assembly 22 are referred to with reference numerals incremented by 200 in the description below. In some embodiments, modular filler needle assembly 222 is provided with a smaller gauge of needle (i.e. a needle having a larger diameter) than modular needle assembly 22, to make it easier to load medicament into medicament chamber 32.

In some embodiments, the needle 226 of modular filler needle assembly 222 is an 18 to 21 gauge needle. Such embodiments may be particularly useful where the medicament to be injected into a patient is particularly thick and/or where a large volume of syringe is used, such that drawing such medicament into medicament chamber 32 using the same gauge of needle as would be used to inject the medicament into a patient would be time-consuming and/or labour intensive.

Because modular filler needle assembly 222 is used only for loading medicament into syringe barrel 30, and not for injecting medicament into a patient, needle 226 will not become contaminated with bodily fluids in the ordinary course of use. Furthermore, in some embodiments, needle 226 is provided with a blunt end, as shown in the illustrated embodiment. Thus, needle 226 can relatively safely be disposed of by simply capping needle 226 and removing it from syringe barrel 30, and needle 226 does not need to be retracted into the syringe. Modular filler needle assembly 222 is therefore not provided with a needle hub 70, unitary propellant release structure 24, or other components used for needle retraction. This simplifies and reduces the cost of manufacture of modular filler needle assembly 222.

The base 382 of modular filler needle assembly 222 is provided with external threads 236, which can engage with threads 38 of syringe body 34. Modular filler needle assembly 222 is also provided with an inwardly tapered portion 266 at its proximal end, which tapers inwardly in the proximal direction from the outer circumference of a support disc 380 provided at the proximal end of modular filler needle assembly 222. Support disc 380 is spaced in the proximal direction away from the base portion 382 of modular filler needle assembly 222 by a projection 384 that is shaped and configured to space support disc 380 a sufficient distance from base portion 382 so that modular filler needle assembly 222 has the same overall dimensions as modular needle assembly 22. This allows modular filler needle assembly 222 to be engaged with syringe body 34. Inwardly tapered portion 266 is engageable with correspondingly tapered portion 68 of syringe body 34, to sealingly engage therewith so that medicament can be drawn into medicament chamber 32.

Needle 226 is supported by the other components of modular filler needle assembly 222 in any suitable manner. For example, in some embodiments, needle 226 is secured to support disc 380 by using suitable adhesives. In some embodiments, needle 226 is secured to support disc 380 by a press fit, or needle 226 may be crimped in, cemented to or otherwise securely fixed to support disc 380 or other components of modular filler needle assembly 222. In some embodiments, needle 226 is insert molded with other components of modular filler needle assembly 222 to create a single component.

In some embodiments, modular filler needle assembly 222 includes features for engaging with a cap to cover needle 226. In some embodiments, these features are the same as those present on modular needle assembly 22. For example, in the illustrated embodiment, modular filler needle assembly 222 includes ribs 330 and snap projections 326 (FIG. 12) for engaging with channels 124 and snap depressions 128 in a cap 27, so that needle 226 can be covered using a cap 27 that is the same as that used to cover needle 26.

In some embodiments, a kit for injecting medicament into a patient using a modular retractable needle assembly is provided. The kit has at least one syringe body 34 having any desired volume, a modular filler needle assembly 222, and a modular needle assembly 22. In some embodiments, the kit has a plurality of syringe bodies 34 having different volumes, a modular filler needle assembly 222, and a modular needle assembly 22. A user can select a syringe body 34 having a desired volume for a particular task, optionally use modular filler needle assembly 222 to fill that syringe body 34 with medicament for injection into a patient, remove and discard modular filler needle assembly (for example including a step of covering used needle 226 with a cap 27 before removing and discarding it, which in some embodiments provides additional grip to remove needle 226 by virtue of the engagement of ribs 330 and snap projections 326 with channels 124 and snap depressions 128 in a cap 27), engage modular needle assembly 22 with the filled syringe body 34 and inject medicament into a patient, and finally retract needle 26 of modular needle assembly 22 as described above. The needles used on modular filler needle assembly 222 and modular needle assembly 22 can have any selected diameter (i.e. be of any gauge) as suited to a given task to be performed.

Figure 14:
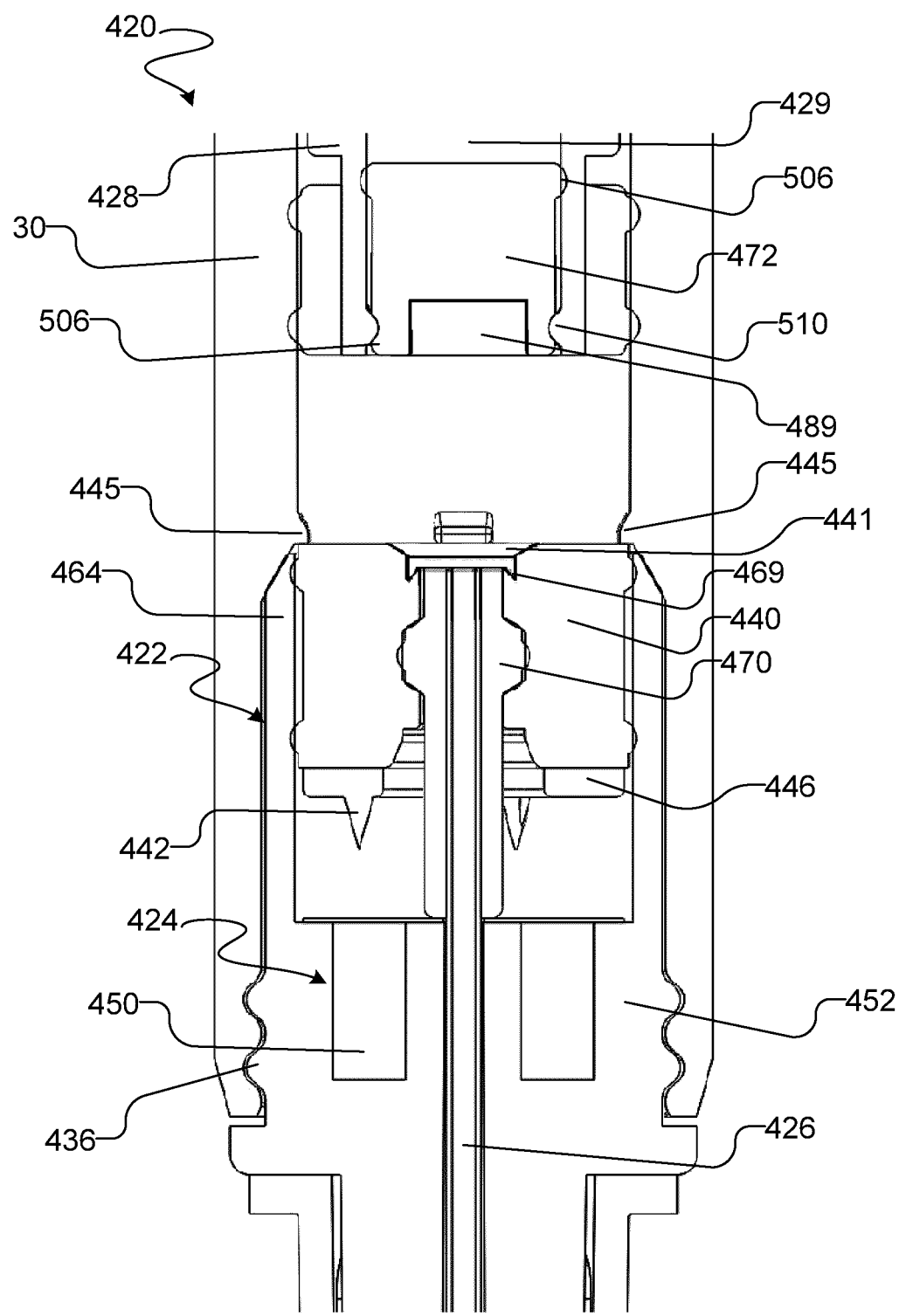
FIG. 14 is a partial cross-sectional view of a further example embodiment of a modular retractable needle assembly.

In alternative embodiments, other structures can be used in place of needle hub 70 and locking tip 72 to form a needle retraction assembly to retract needle 26. For example, as illustrated in FIG. 14 in which reference numerals referring to elements that are the same as in retractable-needle syringe 20 have been incremented by 400, in modular needle assembly 422, needle hub 470 is generally similar to needle hub 70, except that the proximal portion thereof is modified as described below to engage with locking tip 472 in a manner different from the way that needle hub 70 and locking tip 72 engage. The function of locking tip 472 is somewhat similar to locking tip 72, but the distal portion thereof is modified as described below.

The proximal end of needle hub 470 is provided with one or more barbs 469. In the illustrated embodiment, barbs 469 project radially outwardly and in a distal direction from the central axis of needle hub 470. Needle hub 470 does not have a generally cylindrical locking element with a locking edge like locking edge 94 of needle hub 70. In some embodiments, barbs 469 are provided as a fully revolved feature extending fully around the outer perimeter of the proximal portion of needle hub 470. In some embodiments, barbs 469 are provided as one or a plurality of discrete features around the outer perimeter of the proximal portion of needle hub 470. It will be clear to those skilled in the art that the position of barbs 469 at the proximal end of needle hub 470 and the exact configuration of barbs 469 is not essential, as long as barbs 469 are positioned on needle hub 470 so that they can engage with locking tip 472 as described below.

Barbs 469 are positioned and configured so that when locking tip 472 is forced over the proximal portion of needle hub 470 by the application of a post-injection force, barbs 469 bite into the relatively softer material from which locking tip 472 is formed, thereby securing locking tip 472 and needle hub 470 to provide a needle retraction assembly. The engagement between the proximal portion of needle hub 470 and the relatively softer material of locking tip 472 provides a sufficient seal to allow for needle retraction and to prevent further flow of medicament through the needle.

Additionally, because barbs 469 are provided on needle hub 470, locking tip 472 is formed as a single component made from a material into which barbs 469 can engage or bite (e.g. from silicone, an elastomer, or other suitable polymer), rather than being formed as two components, one relatively rigid and one more flexible, as is the case for locking tip 72. The material from which needle hub 470 is made should be more rigid than the material from which locking tip 472 is made, to facilitate barbs 469 engaging with locking tip 472 as aforesaid.

Because needle hub 470 is provided with barbs 469, the distal portion of locking tip 472 does not have special structural features on its inside surface (e.g. similar to locking channel 88 or central cylindrical projection 112) for engagement with needle hub 470. Locking tip 472 is formed so that barbs 469 can engage with the interior surface thereof. For example, in the illustrated embodiment, a central indentation 489 is provided at the distal end of locking tip 472. Central indentation 489 is positioned and configured to receive the proximal end of needle hub 470, so that barbs 469 can bite radially outwardly into the material of locking tip 472 within central indentation 489. The features of the outer edges of locking tip 472 that sealingly engage with the interior of retraction lumen 429, including sealing rings 506, are the same as described for locking tip 472.

To secure locking tip 472 within the distal tip of plunger 428, in some embodiments, including the illustrated embodiment, one of the sealing rings 506 is initially positioned distally of capture projections 510, to prevent movement of locking tip 472 during the application of a loading force or an injection force, but this engagement is broken by the application of a post-injection force (when locking tip 472 is ultimately restrained against further movement in the distal direction by needle hub 470), so that locking tip 472 (and therefore the needle retraction assembly carrying needle 426) can be retracted within retraction lumen 429.

The force required to engage barbs 469 with locking tip 472 should be less than the force required to disengage the engagement of sealing rings 506 and capture projections 510 and displace the vacuum seal securing locking tip 472 in place, to facilitate reliable needle retraction.

The operation of retractable-needle syringe 420 is generally as described for retractable-needle syringe 20, except that the sealing engagement between the locking tip 472 and needle hub 470 is provided by the engagement of barbs 469 with the relatively softer material of locking tip 472 upon the application of a post-injection force by a user.

Suitable materials for the manufacture of modular needle assemblies and retractable needle syringes can be selected by those skilled in the art, and should be selected to be compatible with the medicament to be administered to the subject. For example, the syringe barrel and plunger may be made from any suitable plastic or thermoplastic, for example, polycarbonate, acrylic, copolyester, SBC (styrene-butadiene copolymer) (e.g. Styrolux™), or the like. Any suitable material can be used for the construction of the false wall that allows it to initially retain the needle hub and then release it on the application of a post-injection force. In some embodiments, the false wall is made from an elastomer having a suitable durometer to release the needle hub when a post-injection force is applied. The plunger seal may be made from any suitable material, for example silicone, thermoplastic elastomers, or the like. In some embodiments, the plunger seal is a self-lubricating seal. In some embodiments, the syringe barrel and/or plunger seal are treated with a medical grade lubricant. The needle may be made of medical grade needle tubing. The propellant used in the unitary propellant release structure may be any suitable propellant, for example a pharmaceutical-grade hydrofluorocarbon such as heptafluoropropane, 1,1,1,2-tetrafluoroethane or medical-grade nitrogen. In some embodiments, heptafluoropropane is the propellant, and is selected based on its expansion properties and lack of toxicity.

While a number of exemplary aspects and embodiments are discussed herein, those of skill in the art will recognize certain modifications, permutations, additions and sub-combinations thereof. It is therefore intended that the following appended claims and claims hereafter introduced are not to be limited to the preferred embodiments described herein, but are to be interpreted to include all such modifications, permutations, additions and sub-combinations as are consistent with the broadest interpretation of the specification as a whole.

What is claimed is:

1. A modular retractable needle assembly for engagement with a barrel of a retractable needle syringe having a plunger, the modular retractable needle assembly comprising:
    a body having an upper chamber at a proximal end thereof;
    a propellant chamber defined within the body, the propellant chamber having an inside wall and an outside wall provided by the body;
    a seal sealingly engaged over an upper proximal edge of each of the inside wall and the outside wall of the propellant chamber to seal a propellant in the propellant chamber;
    a retention member initially engaged within the upper chamber, the retention member being moveable in a distal direction in response to an application of a post-injection force to the plunger by a user;
    a needle hub initially engaged within the retention member, the needle hub being engageable with a retractable locking tip of the plunger upon the application of the post-injection force to the plunger by the user;
    a needle for injecting medicament into a patient engaged with the needle hub and projecting distally from the body; and
    a rupturing member projecting in the distal direction, the rupturing member being moveable in the distal direction in response to the application of the post-injection force to the plunger by the user to rupture the seal and thereby release propellant into the upper chamber.

2. A modular retractable needle assembly as defined in claim 1, further comprising engagement members on an outer surface of the body for engaging the body with the barrel.

3. A modular retractable needle assembly as defined in claim 2, wherein the engagement members comprise threads.

4. A modular retractable needle assembly as defined in claim 2, wherein the engagement members comprise a Luer lock fitting.

5. A modular retractable needle assembly as defined in claim 1, wherein the propellant chamber comprises a generally cylindrical channel formed in the body, wherein the seal is engaged with upper edges of inner and outer walls defining the channel.

6. A modular retractable needle assembly as defined in claim 5, wherein the upper edges of both the inner and outer walls are located at approximately the same distance in a distal direction from a proximal end of the modular retractable needle assembly.

7. A modular retractable needle assembly as defined in claim 1, wherein the propellant chamber is positioned distally of the upper chamber, and wherein the upper chamber contains the retention member.

8. A modular retractable needle assembly as defined in claim 1, wherein a proximal end of the upper chamber comprises a tapered sealing surface for sealingly engaging a correspondingly tapered surface provided proximate a distal end of the barrel.

9. A modular retractable needle assembly as defined in claim 1, comprising a cap for covering the needle, an outer surface of the body comprising projections for engaging with corresponding recesses provided in the cap to secure the modular retractable needle assembly against rotational movement within the cap.

10. A kit comprising a modular retractable needle assembly as defined in claim 1 and a modular filler needle assembly for engagement with the barrel of the syringe, the modular filler needle assembly comprising:
   a base engageable with the barrel;
   a support disc spaced apart from the base and positioned to provide a sealing engagement with the barrel; and
   a filler needle supported on the support disc for loading medicament into the syringe, the filler needle projecting distally from the base.

11. A kit as defined in claim 10, wherein the base comprises engagement members on an outer surface of the base for engaging with the barrel.

12. A kit as defined in claim 11, wherein the engagement members comprise threads.

13. A kit as defined in claim 11, wherein the engagement members comprise a Luer lock fitting.

14. A kit as defined in claim 10, wherein the support disc comprises a proximal tapered sealing surface for sealingly engaging a correspondingly tapered surface provided proximate a distal end of the barrel.

15. A kit as defined in claim 10, wherein the filler needle comprises a blunt needle.

16. A kit as defined in claim 10, wherein the support disc is spaced apart from the base by a sufficient distance to allow the modular filler needle assembly to be secured on a syringe having a distal cavity for receiving a modular retractable needle assembly.

17. A kit comprising a modular retractable needle assembly as defined in claim 1 and a syringe, the syringe comprising:
   a barrel;
   a plunger slideable within the barrel for loading or injecting medicament from a medicament chamber of the barrel, the plunger having a retraction lumen therein for receiving a needle retracted from the modular retractable needle assembly;
   a locking tip initially engaged within the retraction lumen, the locking tip being engageable with a needle hub of the modular retractable needle assembly upon application of a post-injection force by a user, the locking tip being retractable into the retraction lumen when a propellant chamber of the modular retractable needle assembly is ruptured; and
   a recess at a distal end of the barrel for receiving the modular needle assembly.

18. A kit as defined in claim 17, comprising threaded grooves in the recess, the threaded grooves being engageable with a correspondingly threaded surface of the modular needle assembly or the modular filler needle assembly.

19. A kit as defined in claim 18, wherein the threaded grooves comprise recessed threaded grooves.

20. A kit as defined in claim 17, further comprising a modular filler needle assembly, the modular filler needle assembly comprising:
   a base engageable with the barrel;
   a support disc spaced apart from the base and positioned to provide a sealing engagement with the barrel; and
   a filler needle supported on the support disc for loading medicament into the syringe, the filler needle projecting distally from the base.

* * * * *